US011996199B2

(12) United States Patent
Seguin

(10) Patent No.: US 11,996,199 B2
(45) Date of Patent: May 28, 2024

(54) SYSTEMS AND METHODS FOR AUTOMATED MEDICAL MONITORING AND/OR DIAGNOSIS

(71) Applicant: Jacques Seguin, London (GB)

(72) Inventor: Jacques Seguin, London (GB)

(*) Notice: Subject to any disclaimer, the term of this patent is extended or adjusted under 35 U.S.C. 154(b) by 0 days.

(21) Appl. No.: 17/466,956

(22) Filed: Sep. 3, 2021

(65) Prior Publication Data

US 2023/0076361 A1  Mar. 9, 2023

(51) Int. Cl.
| | | |
|---|---|---|
| *G16H 50/20* | (2018.01) | |
| *A61B 5/0205* | (2006.01) | |
| *G06F 21/60* | (2013.01) | |
| *G06Q 20/38* | (2012.01) | |
| *G16H 10/60* | (2018.01) | |
| *G16H 40/67* | (2018.01) | |
| *A61B 5/00* | (2006.01) | |
| *A61B 5/024* | (2006.01) | |

(52) U.S. Cl.
CPC ........... *G16H 50/20* (2018.01); *A61B 5/0205* (2013.01); *G06F 21/602* (2013.01); *G06Q 20/389* (2013.01); *G16H 10/60* (2018.01); *G16H 40/67* (2018.01); *A61B 5/0077* (2013.01); *A61B 5/024* (2013.01)

(58) Field of Classification Search
CPC ........ G16H 50/20; G16H 40/67; G16H 10/60; G16H 20/30; G16H 20/00; G16H 50/30; G16H 50/50; G16H 80/00; A61B 5/025; G06F 21/602; G06Q 20/389
USPC ...................................................... 705/2–3
See application file for complete search history.

(56) References Cited

U.S. PATENT DOCUMENTS

| | | | |
|---|---|---|---|
| 5,839,438 A | 11/1998 | Graettinger et al. | |
| 9,993,163 B2 | 6/2018 | Krauss et al. | |
| 11,462,327 B2 | 10/2022 | Ohnemus et al. | |
| 2004/0103001 A1 | 5/2004 | Mazar et al. | |
| 2007/0143215 A1 | 6/2007 | Willems | |

(Continued)

FOREIGN PATENT DOCUMENTS

| | | |
|---|---|---|
| WO | WO-2005084534 A1 | 9/2005 |
| WO | WO-2020005815 A1 | 1/2020 |

OTHER PUBLICATIONS

Abo-Zahhad M, Ahmed SM, Elnahas O. A wireless emergency telemedicine system for patients monitoring and diagnosis. Int J Telemed Appl. 2014;2014:380787. doi: 10.1155/2014/380787. Epub May 6, 2014. PMID: 24883059; PMCID: PMC4026975 (Year: 2014).*

(Continued)

*Primary Examiner* — Joseph D Burgess
(74) *Attorney, Agent, or Firm* — Eversheds Sutherland (US) LLP; Christopher C. Bolten; Robert D. Ward

(57) ABSTRACT

Systems and methods are provided involving various medical monitoring and/or diagnostic systems. The monitoring and diagnostic systems may involve one or more connected devices (e.g., a smart watch and/or other sensor device) and may continuously monitor an individual and analyze physiological and other data to determine a medical device, condition or event has occurred. The monitoring and diagnostic systems may be a guided self-examination system for determining a medical diagnosis, condition or event. The medical monitoring and diagnostic systems may even be specific to a family or individuals in a certain geographic location.

21 Claims, 14 Drawing Sheets

(56) References Cited

U.S. PATENT DOCUMENTS

| | | | |
|---|---|---|---|
| 2008/0147554 A1* | 6/2008 | Stevens | G16H 10/60 705/51 |
| 2008/0201172 A1 | 8/2008 | McNamar | |
| 2014/0081654 A1* | 3/2014 | Bechtel | G16H 40/63 705/2 |
| 2014/0257058 A1 | 9/2014 | Clarysse et al. | |
| 2017/0303846 A1* | 10/2017 | O'Brien | A61B 5/0075 |
| 2018/0114591 A1* | 4/2018 | Pribanic | G16H 70/20 |
| 2018/0158551 A1 | 6/2018 | Bradley et al. | |
| 2018/0218123 A1* | 8/2018 | Gomez Sanchez | G16H 50/20 |
| 2018/0253464 A1* | 9/2018 | Kohli | G06F 16/219 |
| 2019/0065970 A1 | 2/2019 | Bonutti et al. | |
| 2019/0134396 A1 | 5/2019 | Toth et al. | |
| 2019/0371453 A1* | 12/2019 | Larkin | G16H 10/60 |
| 2020/0029837 A1 | 1/2020 | Joudi | |
| 2020/0146550 A1* | 5/2020 | Tunnell | H04L 65/4015 |
| 2020/0342979 A1* | 10/2020 | Sadowsky | A61B 5/165 |
| 2021/0012894 A1 | 1/2021 | Zelocchi | |
| 2021/0020294 A1* | 1/2021 | Bharmi | G16H 50/30 |
| 2021/0241869 A1 | 8/2021 | Muse et al. | |
| 2021/0295992 A1* | 9/2021 | Al-Sinan | G06Q 20/16 |
| 2021/0319914 A1 | 10/2021 | Roh | |
| 2022/0054794 A1 | 2/2022 | Gurumoorthy | |
| 2022/0384001 A1* | 12/2022 | Gnanasambandam | G16H 10/20 |

OTHER PUBLICATIONS

M. Gandhi, V. K. Singh and V. Kumar, "IntelliDoctor—AI based Medical Assistant," 2019 Fifth International Conference on Science Technology Engineering and Mathematics (ICONSTEM), Chennai, India, 2019, pp. 162-168, doi: 10.1109/ICONSTEM.2019.8918778 (Year: 2019).*

Boonstra, A., Information Management in Professional Organisations: Alternative Approaches to the Application of Information Systems in Professional Organisations, University of Glasgow (United Kingdom) (1995).

International Search Report & Written Opinion dated Dec. 7, 2022 in Int'l PCT Patent Appl. Serial No. PCT/IB2022/058080 (0910).

Schlingman, Jillia, Hospitals in United States and Germany Team Up with Matternet and UPS to Make Medical Laboratory Deliveries by Drone the New Normal; Dark Daily, Aug. 11, 2021, retrieved from the Internet: https://www.darkdaily.com/2021/08/11/hospitals-in-united-states-and-germany-team-up-with-matternet-and-ups-to-make-medical-laboratory-deliveries-by-drone-the-new-normal [retrieved on Nov. 28, 2022].

Wikipedia, "Brain-computer Interface," dated Jul. 24, 2021, Retrieved from the Internet:, https://en.wkipedia.org/w/index.php?title_Brain-computer_interface&oldid=1035169840 [retrieved on Nov. 28, 2022].

Boonstra, A. Information management in professional organisations: Alternative approaches to the application of information systems in professional organisations (Order No. 10391319). Available from ProQuest Dissertations and Theses Professional. (1874565783). 349 Pages (Mar. 1995).

* cited by examiner

SYSTEMS AND METHODS FOR AUTOMATED MEDICAL MONITORING AND/OR DIAGNOSIS

TECHNICAL FIELD

The present invention generally relates to the field of preventative medicine and medical analysis, monitoring, and/or diagnosis. For example systems and methods are provided herein for performing automated medical diagnoses and/or detecting various medical conditions and/or events based on physiological data and related medical information.

BACKGROUND

As the world becomes more connected and access to the Internet continues to grow, individuals from locations across the globe have access to information and services through the use of connected devices such as mobile phones, tablets, laptops, smart devices, wearable devices and the like. The Internet and connected devices has provided a platform for web-based services such as telemedicine—health related services offered remotely via a connected device (e.g., over the Internet or cellular connection). Telemedicine is a convenient alternative for those seeking health services outside of the traditional doctor's office or hospital setting. In the age of Covid-19, telemedicine has become commonplace as such services permit individuals to speak with healthcare providers without leaving their home.

Telemedicine and similar services are limited in several respects. For example, such telemedicine visits are often accompanied by the same fees as traditional doctor's office visits. Accordingly, if traditional medical care is cost prohibitive to an individual, it is likely that telemedicine will be equally cost prohibitive. Further, while a camera may permit a doctor or other healthcare provider to see the patient, telemedicine visits are devoid of any additional input for the doctor to consider such as tactile input, high resolution and/or magnified viewing, and/or sensor input (e.g., thermometers, blood pressure, oxygen saturation, etc.). For example, auscultation and/or orifice examination and other clinical examination may be difficult or impossible via telemedicine. Telemedicine also can be a time consuming and may require a long wait. Similar to scheduling in-person doctor's visits, telemedicine appointments depend on the healthcare provider's schedule.

In addition to telemedicine, connected devices such as wearable devices, also known as "wearables" may provide health related information. For example, certain smart watches may determine a user's heart rate using various sensors (e.g., using light emitting diodes (LEDs) and photoplethysmography). However, such devices may be limited with respect to input (e.g., may only consider one type of sensor data) and may consider such data isolated from other relevant information about a user such as medical history and/or family history. Further such devices often require a healthcare provider's input to determine a diagnosis or recommend treatment. Also, while medical records and knowledge are well-documented and voluminous, it is difficult to leverage this information to generate meaningful inferences from such information.

Accordingly, there is a need for improved methods and systems for systematically collecting various inputs relevant to an individual's health and further for analyzing the inputs and generating one or more medical diagnoses.

SUMMARY OF THE INVENTION

Provided herein are systems and methods for automated medical monitoring and/or diagnosis. The systems and methods may include one or more user devices and/or sensor devices for determining physiological data of a user which may be processed to determine the presence of a medical condition, event, and/or emergency corresponding to the patient. The user devices and/or sensor devices may alert the user of a detected medical condition, event, and/or emergency. Additionally, the emergency services and/or an emergency contact may be alerted and informed of the medical condition, event and/or emergency. The methods and systems may further include encrypting the physiological data and or information regarding a medical condition, event and/or emergency (e.g., using block chain technology). The methods and systems may also process payments for related services.

A method for determining a medical diagnosis may, in one example, include determining a user profile associated with a user device, a first device, and a second device, requesting first data from the first device, receiving the first data from first device, the first data indicative of first visual data corresponding to a user, requesting second data from the second device, receiving the second data from the second device, the second data indicative of audio data corresponding to the user, determining a first medical diagnosis corresponding to the user based on the first data and the second data using at least one first algorithm trained to determine at least one medical diagnosis, causing the user device to present a message indicating the determined medical diagnosis, and causing one or more of the first device and second device to present instructions corresponding to a user action based on the medical diagnosis.

The method may further include determining that there is a medical emergency corresponding to the medical diagnosis. Determining that there is a medical emergency may include processing the first data and the second data using at least one second algorithm trained to detect a medical emergency. The method may further include sending a second message regarding the medical emergency to one or more of emergency services. The message sent to one or more emergency services may include a location corresponding to the user. The method may further include determining an emergency contact based on the user profile and/or sending a third message regarding the first medical diagnosis to the emergency contact. The method may further include encrypting the third message using blockchain prior to sending the third message to the emergency contact. The method may further include requesting third data from a third device associated with the user profile, and receiving the third data from the third device, the third data indicative of physiological data corresponding to the user. The first medical diagnosis may further be based on the third data.

A computing device for guided medical examination, in one example, may include a memory configured to store computer-executable instructions, and at least one computer processor configured to access the memory and execute the computer-executable instructions to establish a connection with a user device and a sensor device, the user device including a display and a first sensor and the sensor device including a second sensor, cause the user device to present a request to generate visual data using the first sensor, receive first visual data from the first device, the first visual data generated using the first sensor and corresponding to a user, determine a second data type based on the first visual data, determine an action corresponding to the second data type, cause the user device to present instructions for the user to perform the action, send, after causing the user device to present instructions for the user to perform an action, a request for sensor data to the sensor device, the sensor data associated with the second data type, receive first sensor data from the sensor device, the first sensor data generated using the second sensor and corresponding to the action, and determine a medical diagnosis based on the first visual data and first sensor data using one or more algorithms trained to determine medical diagnoses.

The at least one computer processor may further access the memory and execute the computer-executable instructions to send a message to one or more of the user device or the sensor device indicating the medical diagnosis. The first sensor may be a camera and the first visual data may correspond to at least a portion of a face of the user. The second sensor may be a heart rate sensor and the first sensor data may be heart rate data corresponding to the user. The at least one computer processor may be further configured to access the memory and execute the computer-executable instructions to determine a user profile associated with at least the user device. The at least one computer processor may be further configured to access the memory and execute the computer-executable instructions to determine medical history data associated with the user profile, wherein the medical diagnosis is further based on the medical history data.

A method for performing a guided medical examination, may in one example, include establishing a connection with a user device and a sensor device, the user device including a display and a first sensor and the sensor device including a second sensor, causing the user device to present a request to generate visual data using the first sensor, receiving first visual data from the first device, the first visual data generated using the first sensor and corresponding to a user, determining a second data type based on the first visual data, determining an action corresponding to the second data type, causing the user device to present instructions for the user to perform an action, sending, after causing the user device to present instructions for the user to perform an action, a request for sensor data to the sensor device, the sensor data associated with the second data type, receiving first sensor data from the sensor device, the first sensor data generated using the second sensor and corresponding to the action, and determining a medical diagnosis based on the first visual data and first sensor data using one or more algorithms trained to determine medical diagnoses.

The method may further include sending a message to one or more of the user device or the sensor device indicating the medical diagnosis. The first sensor may be a camera and the first visual data may correspond to at least a portion of a face of the user. The second sensor is a heart rate sensor and the first sensor data is heart rate data corresponding to the user. The method may further include determining a user profile associated with at least the user device. The method may further include determining medical history data associated with the user profile, wherein the medical diagnosis is further based on the medical history data.

A method for determining a medical diagnosis corresponding to a user, in one example, may include causing a user device to present a request for symptom information, receiving first symptom information from the user device, the first symptom information indicative of symptoms experienced by the user, determining a first data type associated with a first device and a second data type associated with a second device based on the first symptom information, the first data type different from the second data type, requesting first data from the first device, the first data corresponding to the first data type, receiving the first data generated by the first device, requesting second data from the second device, the second data corresponding to the second data type, receiving the second data generated by the second device, and determining a first medical diagnosis corresponding to the user based on the first data and the second data using at least one first algorithm trained to determine at least one medical diagnosis.

The first data and the second data may be encrypted by the user device. The method may further include decrypting the first data and second data. The method may further include causing the user device to present a display indicating the first medical diagnosis. The first symptom information may include audio data generated by the user device. The method may further include transcribing the audio data. The method may further include transcribing the audio data of the first symptom information. The first data and the second data may be received from the user device. The first medical diagnosis may also be based on the first symptom information. The first data and the second data may be selected from the group consisting of physiological data, blood data, image data, tissue data, body secretion data, breath analyzer data and motion data. The method may further include determining, after receiving the first symptom information, to request second symptom information, causing the user device to present a request for the second symptom information, and receiving the second symptom information from the user device. The method may further include requesting payment information from the user device, and receiving payment information from the user device. The payment information may be secured using at least one blockchain algorithm.

The foregoing summary is illustrative only and is not intended to be in any way limiting. In addition to the illustrative aspects, embodiments, and features described above, further aspects, embodiments, and features will become apparent by reference to the following drawings and the detailed description.

Figure 1:
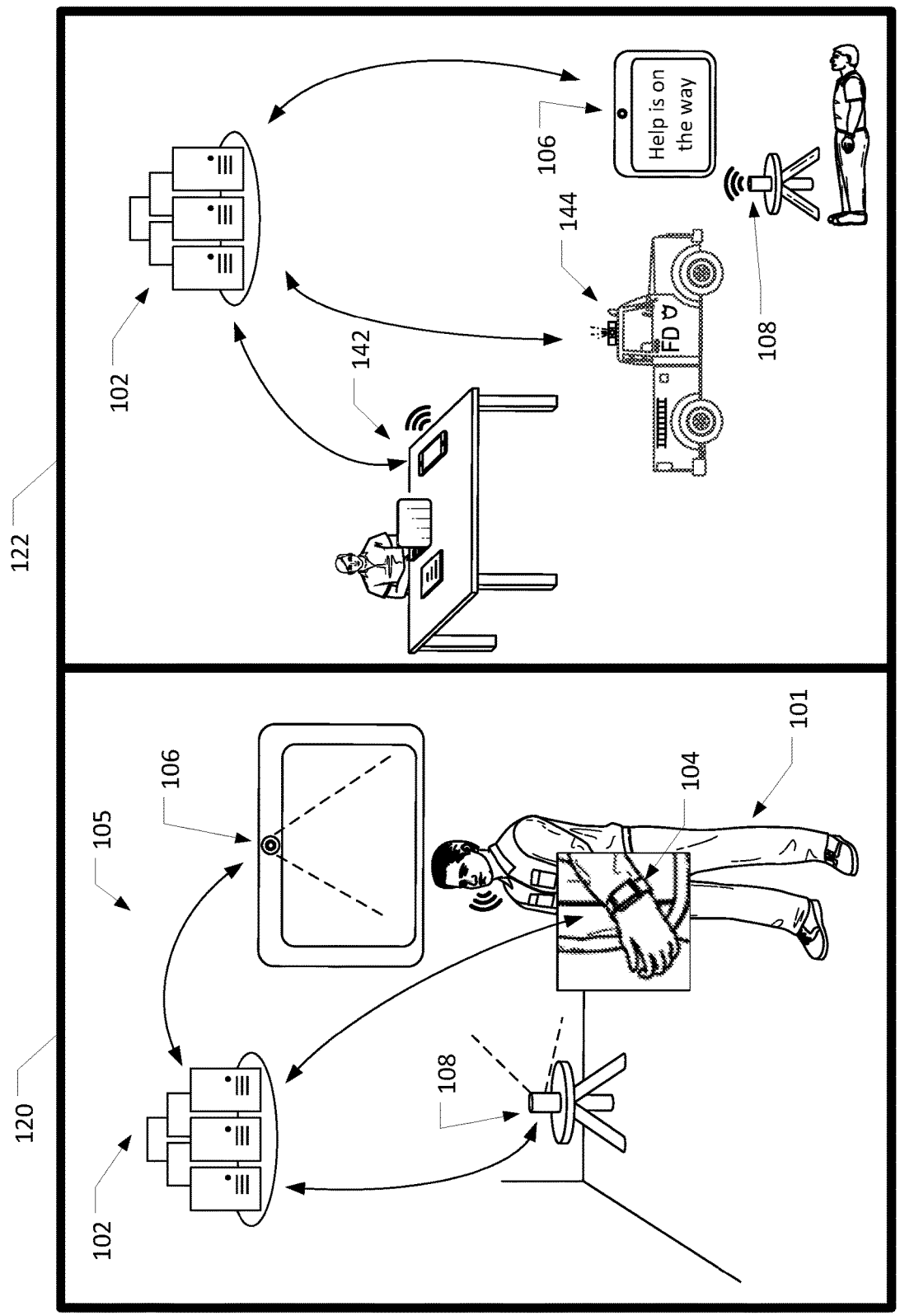
FIG. 1 illustrates an exemplary continuous monitoring system for determining a medical diagnosis, in accordance with some aspects of the present invention.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE INVENTION

The present invention is directed to various medical diagnostic systems for determining one or more medical diagnosis, condition and/or event based on physiological input provided from one or more device. For example a user may use one or more connected devices that may be connected to one or more other computing devices. A connected device may be a mobile phone, smart device, smart sensor, wearable device, tablet, smart television, laptop or desktop computer, or the like. The connected device may collect information about the user's health or body such as image data, video data, voice data, motion data, biological data, body secretion data, breath analyzer data, fingerprint scan, eye (e.g., iris or retina) scan, and/or any other bio-related information about the user, which is referred to as physiological data.

The connected devices may send the physiological data corresponding to the user to a remote computing device (e.g., via the Internet) to be analyzed by the remote computing device, which may be one or more computing devices. The remote computing device may run one or more trained algorithms to analyze the data received from the connected devices, as well as other information such user medical history and/or family medical history, to determine a medical diagnosis or otherwise detect a medical condition or event. The one or more algorithms may be trained models or networks using data corresponding to users associated with a particular diagnosis, condition or event. For example, the one or more algorithms may be one or more trained neural networks.

If the remote computing device processes the data received by the connected devices and determines the presence of one or more medical diagnoses, conditions or events, the computing device may send a message to a connected device associated with the user indicating that a medical diagnosis, condition and/or event was detected. Other devices related to the user (e.g., emergency contacts) and/or medical or emergency services may also receive a message regarding the medical diagnosis, condition or event.

The methods and systems described herein may be automated in that they do not require human intervention. In this manner such systems may provide critical medical information to those individuals who cannot afford traditional healthcare services. Further, such automated systems may inform an individual of a medical diagnosis, condition and/or event in real time or near real time, which may in some cases be the difference between receiving time sensitive emergency services and permanent bodily injury or even death. Such systems and methods may be beneficial for regularly monitoring health parameters and/or prevention or early detection of future diseases.

The methods and systems described herein may enhance the knowledge and/or capabilities of a single physician. For example, the algorithms and machine learning systems described herein may leverage the knowledge and capabilities of multiple physicians as such knowledge and capabilities (e.g., medical knowledge, diagnostic knowledge, and/or therapeutic knowledge) may be used to design, train and/or improve the algorithms and machine learning systems.

Referring now to FIG. 1, exemplary monitoring and diagnostic system 105 is illustrated. Monitoring and diagnostic system 105 is designed to monitor an individual situated in a certain area such as a room or facility or otherwise situated near monitoring devices. Monitoring and diagnostic system 105 may include one or more monitoring devices that may each be a connected device (e.g., connected to the Internet or other well-known wireless network such as cellular). For example, monitoring and diagnostic system 105 may include sensor device 104, visual device 106 and audio device 108. Each of sensor device 104, visual device 106 and audio device 108 may communicate either directly or indirectly (e.g., via a router) with computing device 102 which may be remote in that computing device 102 may be situated a far distance from sensor device 104, visual device 106 and audio device 108.

Computing device 102 may be any computing device that may communicate with sensor device 104, visual device 106 and audio device 108, one or more servers and/or other computing devices or connected devices, via any well-known wired or wireless system (e.g., Wi-Fi, cellular network, Bluetooth, Bluetooth Low Energy (BLE), near field communication protocol, etc.). Computing device 102 may be any computing device with one or more processor. In the example illustrated in FIG. 1, computing device 102 may be server, desktop or laptop computer, or the like. Computing device 102 may run one or more local applications to facilitate communication between computing sensor device 104, visual device 106 and audio device 108 and/or any other computing devices or servers and otherwise process instructions and/or perform operations described herein. The local application may be one or more applications or modules run on and/or accessed by computing device 102.

Sensor device 104 may be any computing device that may communicate with at least computing device 102, either directly or indirectly, via any well-known wired or wireless system. Sensor device 104 may be any well-known smart sensor and/or computing device incorporating or coupled to one or more sensors and may further include one or more processor. For example, sensor device 104 may be a smart watch or any other wearable-type device, that may include one or more camera, microphone, optical sensor (e.g., photodiode), accelerometer, heart rate sensor, thermometer, blood glucose sensor, biometric sensor (e.g., face, fingerprint, eye, iris or retina, DNA scanner or analyzer), keystroke sensor, humidity sensor, breath analyzer, ECG sensor, voice analyzer, pressure sensor, and/or any other well-known sensor. Further, sensor device 104 may include one or more display (touch-screen display), speaker, or any other well-known output device. Sensor device 104 may be a sensor available from LifeLens Technologies, LLC of Ivyland, PA such as a sensor described in U.S. Patent Application Pub. No. 2019/0134396 to Toth et al, the entire contents of which are incorporated herein by reference.

Visual device 106 may be any computing device that may communicate with at least computing device 102, either directly or indirectly, via any well-known wired or wireless system. Visual device 106 may be any well-known computing device that may incorporate a camera or other visual detection technology (e.g., infrared sensor) and may further include one or more processor. Visual device 106 may optionally include one or more inputs (e.g., buttons) and/or one or more output (e.g., display). For example, visual device 106 may be smart television that may include a camera.

Audio device 108 may be any computing device that may communicate with at least computing device 102, either directly or indirectly, via any well-known wired or wireless system. Visual device 108 may be any well-known computing device that may incorporate a microphone or other audio detection technology and may further include one or more processor. For example, visual device 108 may be smart speaker that may include a microphone. Visual device 108 may include one or more inputs (e.g., buttons) and/or one or more outputs (e.g., speaker).

It is understood that additional or fewer devices (e.g., connected devices) than those shown in FIG. 1 may be included in diagnostic system 105 and/or audio device 106 and visual device 108 may be the same device. It is further understood that each of sensor device 104, visual device 106 and audio device 108 may communicate with one another and/or one or more of sensor device 104, visual device 106 and audio device 108 may communicate with computing device 102 via one of sensor device 104, visual device 106 and audio device 108 (e.g., sensor device 104 may communicate with computing device 102 via audio device 108). In an alternative arrangement, computing device 102 may be a local device (e.g., in the same area as user 101) and/or may be incorporated into sensor device 104, visual device 106 and/or audio device 108.

As shown in setting 120 of FIG. 1, sensor device 104, visual device 106 and audio device 108 may each be situated in a room. A user (e.g., user 101) may also be situated in the room. The user may be wearing sensor device 104, which may be a smart watch. As shown in setting 120, user 101 may be in view of visual device 106 and may further be close enough to audio device 108 and visual device 106 such that audio device 108 and visual device 106 may capture images and sounds of user 101, respectively. Visual device 106 and audio device 108 may send the captured visual data and audio data to computing device 102 (e.g., via the Internet). Such data may be continuously and/or periodically captured and sent to computing device 102.

Sensor device 104 may also capture and/or obtain sensor data corresponding to the user 101. For example, sensor 104 may include a heart rate sensor and a temperature sensor and heart rate data and temperature data may be continuously and/or periodically sent to computing device 102. It is understood, however, the sensor device 104 may send any other sensor data to computing device 102. In this manner, computing device 102 may receive sensor data from sensor device 104, visual data including images of user 101 from visual device 106 and audio data including audible sounds from user 101 from audio device 108.

Computing device 102 may receive the sensor data, visual data, and/or audio data and may process the data received from the connected device using one or more algorithms designed and/or trained to determine a medical diagnosis, condition and/or event. For example, the one or more algorithms may employ, form and/or incorporate one or more models and/or neural networks to make this determination. Neural networks may learn from raw or preprocessed data and may be trained using known inputs (e.g., inputs with known medical diagnoses, conditions and/or events). It is further understood that data and determined medical diagnoses, conditions and/or events may be used to improve and/or further train the one or more algorithms.

As shown in setting 122, if computing device 102 determines the presence and/or a risk (e.g., above a predefined threshold) of a medical diagnosis, condition, or event, computing device 102 may inform one or more devices of such medical diagnosis, condition, or event and/or may cause one or more connected device to present such information. For example, computing device 102 may send an alert to device 142 which may be known to computing device 102 to be an emergency contact of user 101.

Additionally, or alternatively, computing device 102 may send an alert or similar message to emergency services 144. Such alert or message may include the location of user 101, information about the medical diagnosis, condition, or event, information about the position of the patient (e.g., whether the patient is sitting, lying down, crouching, etc.), location of user (e.g., address and/or GPS coordinates) and/or any other relevant information. Also, computing device 102 may optionally cause one or more connected device (e.g., visual device 106 and audio device 108) to present information about the medical diagnosis, condition, or event and/or or other relevant information (e.g., emergency medical advice and/or treatment instructions). In one example, computing device 102 may cause visual device 106 and/or audio device 108 to present a message that "help is on the way" and/or instructions to perform an action (e.g., lay down). In yet another example, computing device 102 may permit emergency services 144 to control connected devices (e.g., visual device 106 and audio device 108) and cause such devices to present information and/or view the user using such devices.

Figure 2:
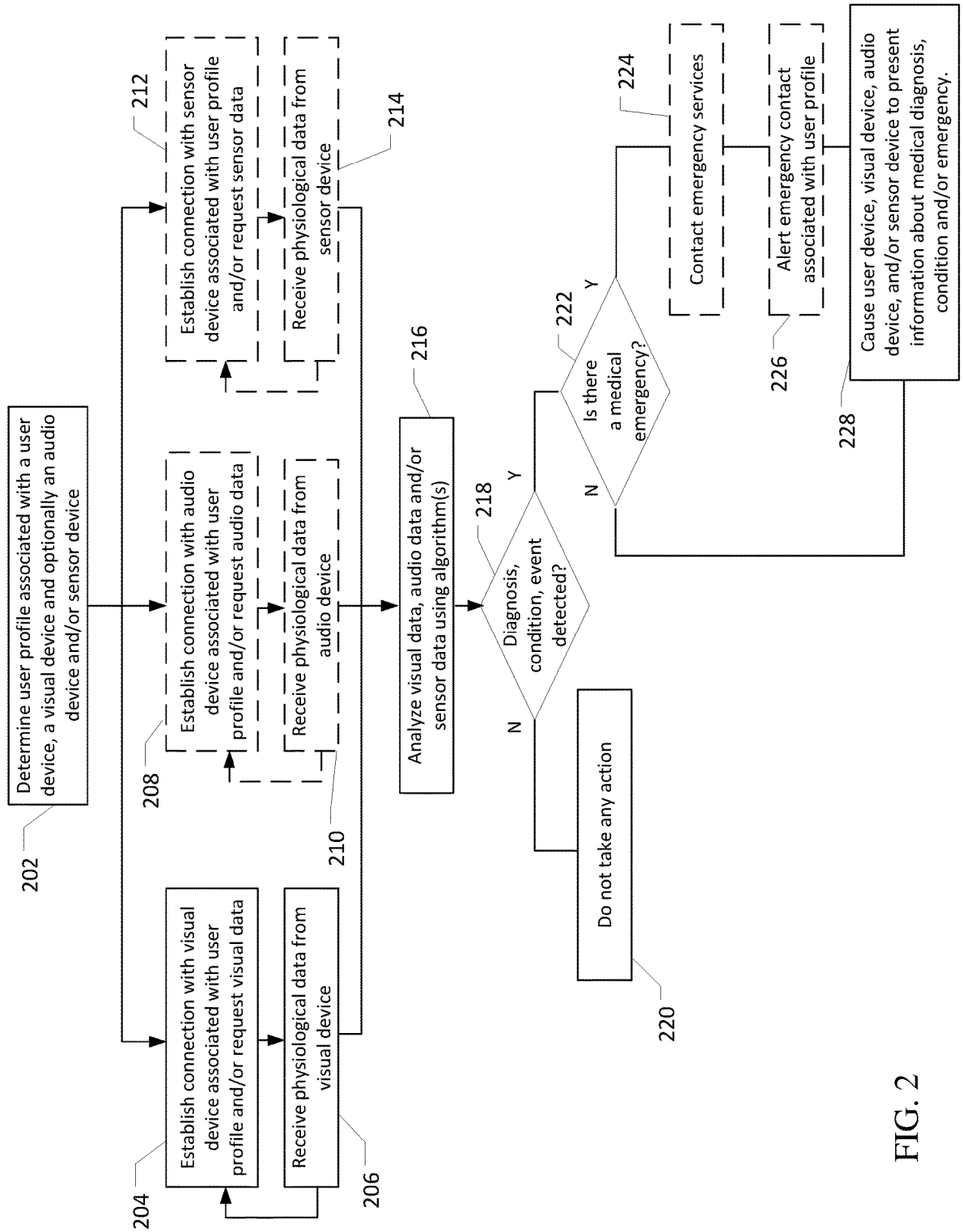
FIG. 2 illustrates an exemplary process flow for continuous monitoring and determining a medical diagnosis.

Referring now to FIG. 2, an example process flow for determining visual, audio, and/or sensor data is depicted, in accordance with one or more example embodiments of the present disclosure. Some or all of the blocks of the process flows in this disclosure may be performed in a distributed manner across any number of devices (e.g., computing devices, user devices and/or servers). Some or all of the operations of the process flow may be optional and may be performed in a different order.

At block 202, computer-executable instructions stored on a memory of a device, such as a computing device, may be executed to determine a user profile associated with one or more connected device (e.g., a user device, a visual device and optionally an audio device and/or sensor device). At block 204, computer-executable instructions stored on a memory of a device, such as a computing device, may be executed to establish a connection with a visual device (e.g., smart television) associated with the user profile and/or request visual data from the visual device. At block 206, computer-executable instructions stored on a memory of a device, such as a computing device, may be executed to receive physiological data from the visual device. The physiological data may include images of an area, which may include images of a user or other individual. Blocks 204 and 206 may be continuously and/or periodically initiated to continuously and/or periodically send physiological data to the computing device.

At optional block 208, computer-executable instructions stored on a memory of a device, such as a computing device, may be executed to establish a connection with an audio device (e.g., smart speaker) associated with the user profile and/or request audio data from the audio device. At optional block 210, computer-executable instructions stored on a memory of a device, such as a computing device, may be executed to receive physiological data from the audio device. The physiological data may include sounds from an area, which may include sounds of a user or other individual. Blocks 208 and 210 may be continuously and/or periodically initiated to continuously and/or periodically send physiological data to the computing device.

At optional block 212, computer-executable instructions stored on a memory of a device, such as a computing device, may be executed to establish a connection with a sensor device (e.g., smart watch) associated with the user profile and/or request physiological data from the smart device. At optional block 214, computer-executable instructions stored on a memory of a device, such as a computing device, may be executed to receive physiological data from the sensor device. The physiological data may include sensor data corresponding to the user (e.g., heart rate data). Blocks 212 and 214 may be continuously and/or periodically initiated to continuously and/or periodically send sensor data to the computing device.

At block 216, computer-executable instructions stored on a memory of a device, such as a computing device, may be executed to analyze the physiological data (e.g., visual, audio and/or sensor data) using one or more algorithms designed and/or trained to detect one or more medical diagnosis, condition, and/or event. The physiological data may be optionally decrypted at block 216. For example, the data received at blocks 206, 210 and/or 214 may be encrypted using any well-known encryption techniques (e.g., well-known asymmetric and/or symmetric encryption techniques). In one example, asymmetric cryptography and/or digital signatures generated using blockchain may be employed to decrypt the data received at blocks 206, 210 and/or 214 and to decrypt the data at block 216. Asymmetric cryptography uses key pairs (e.g., public key and/or private key) which may be required to secure and/or access data. Blockchain algorithms and/or technology may be used to secure data and/or create digital signatures that must be present to decrypt the data. In one example, blockchain technology may be used to permit access to and/or decrypt data if a certain number of keys of a predefined number of keys are provided (e.g., 2 out of 3 total keys).

As explained above, the trained algorithms may be one or more models and/or neural networks. At decision 218, computer-executable instructions stored on a memory of a device, such as a computing device, may be executed to determine if a medical diagnosis, condition and/or event has been detected or the presence of one of the following has satisfied a predetermined threshold. While this determination may be automated without any human assistance or input, the system may optionally request input and/or confirmation from a healthcare provider. Additionally, or alternatively, the system may optionally request that a healthcare provider confirm the medical diagnosis, condition and/or event.

If a medical diagnosis, condition and/or event has not been detected or the presence of one of the following has not satisfied a predetermined threshold, no further action may be taken. Alternatively, if a medical diagnosis, condition and/or event has been detected or the presence of one of the following has satisfied a predetermined threshold, at decision 222 computer-executable instructions stored on a memory of a device, such as a computing device, may be executed to determine if there is a current medical emergency (e.g., does the user need immediate medical attention). The one or more algorithms may be trained to make this determination.

If a medical emergency is detected, at optional block 224 computer-executable instructions stored on a memory of a device, such as a computing device, may be executed to contact emergency services. Additionally, or alternatively, at optional block 226 computer-executable instructions stored on a memory of a device, such as a computing device, may be executed to alert an emergency contact associated with the use profile of the medical emergency. Further, whether or not a medical emergency is detected, at block 228, computer-executable instructions stored on a memory of a device, such as a computing device, may be executed to cause the user device, visual device, audio device, and/or sensor device to present information about the medical diagnosis, condition, and/or emergency. Information about the medical diagnosis, condition, and/or emergency may be optionally encrypted at block 224, 226 and/or 228 using any well-known encryption techniques (e.g., well-known asymmetric, symmetric and/or blockchain encryption techniques).

Figure 3:
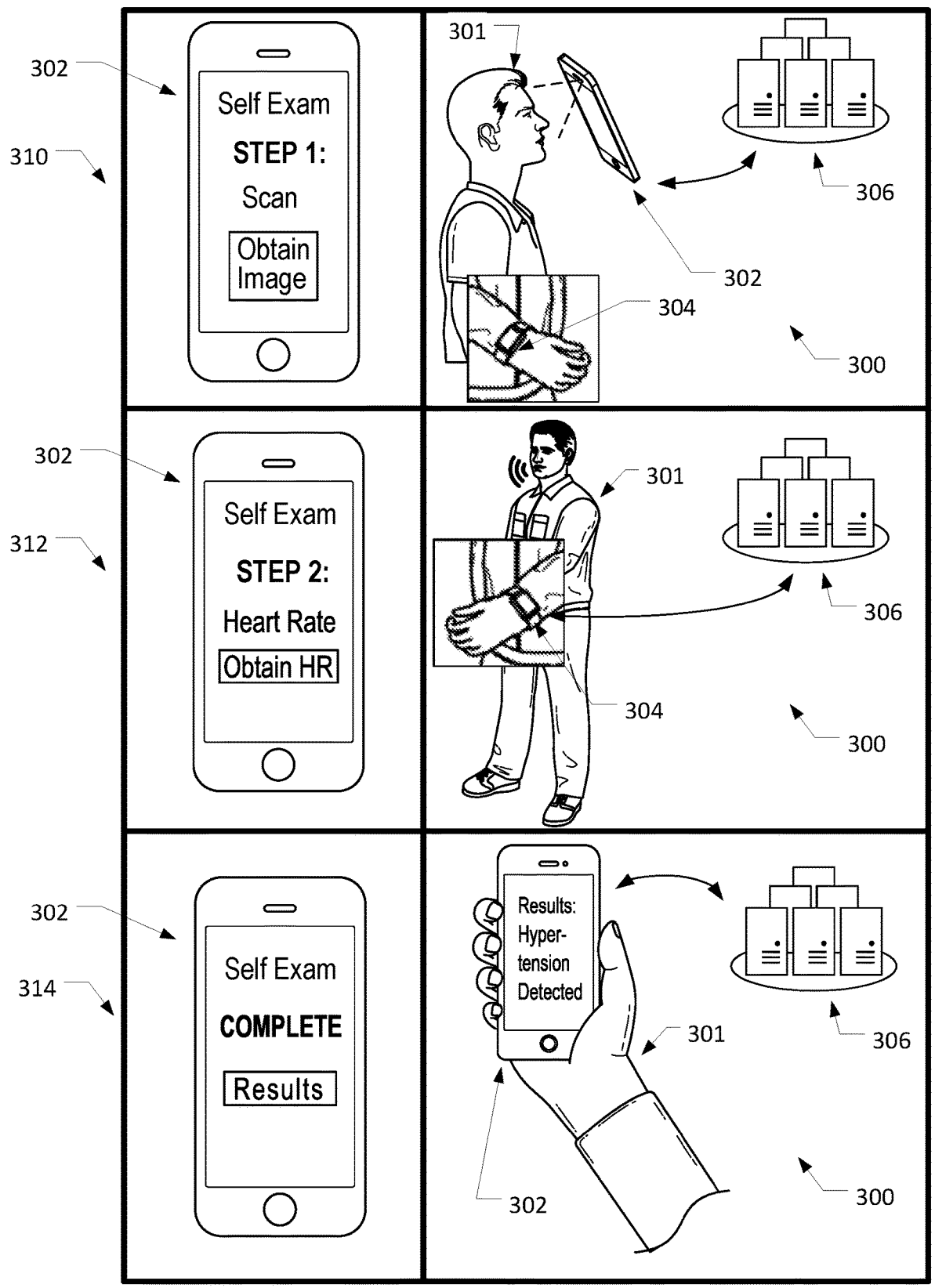
FIG. 3 illustrates an exemplary guided self-examination system for determining a medical diagnosis

Referring now to FIG. 3, an exemplary guided self-examination system is illustrated in accordance with the present disclosure. Self-examination system 300 may include user device 302, sensor device 304, and/or computing device 306. Sensor device 304 and computing device 306 may be the same as or similar to sensor device 104 and computing device 102 described above with respect to FIG. 1, respectively. User device 302 may be any computing device that may communicate with sensor device 304, computing device 306, and/or any other connected devices, servers and/or other computing devices or user devices, via any well-known wired or wireless system (e.g., Wi-Fi, cellular network, Bluetooth, Bluetooth Low Energy (BLE), near field communication protocol, etc.).

User device 302 may be any computing device with one or more processor and/or one or more sensor (e.g., a camera). In the example illustrated in FIG. 2, user device 302 may be a smart phone, tablet, e-reader laptop, desktop computer, or the like. User device 302 may run one or more local applications to facilitate communication between computing device 306, sensor device 304, and/or any other computing devices or servers and otherwise process instructions and/or perform operations described herein. The local application may be one or more applications or modules run on and/or accessed by user device 302.

Each of user device 302, sensor device 304, and computing device 306 may communicate either directly or indirectly with one another. It is understood that additional or fewer devices (e.g., connected devices) than those shown in FIG. 3 may be included in self-examination system 300. In an alternative arrangement, computing device 306 may be a local device (e.g., in the same area as user 301) and/or may be incorporated into sensor device 104, visual device 106 and audio device 108.

As shown in setting 310 of FIG. 3, user device may present "Step 1" of a "Self Exam." In the example illustrated in setting 310, Step 1 may involve a "Scan" and may include a button on a user interface to capture an image on the user device. As shown in setting 310, user 301 may orient a camera on user device 302 towards a certain area of user 301 (e.g., face, mouth, eye, etc.) to obtain an image that may be sent to computing device 306 for analysis on computing device 306. For example, an image of the eye may be used to determine eye pressure and/or perform a retina evaluation.

As shown in setting 312 of FIG. 3, user device may present "Step 2" of the "Self Exam" which may include determining a "heart rate" and may further include a button on a user interface to capture the heart rate on a sensor device. As shown in setting 312, computing device 306 may instruct sensor device 304 to determine heart rate data on sensor device 304. Sensor device 304 may then send the heart rate data to computing device 306 for analysis on computing device 306.

Computing device 306 may analyze the data received from the user device, sensor device, and/or any other connected devices. For example, computing device 306 may execute one or more algorithms trained and/or designed to determine a medical diagnosis, condition or event based on the received data. It is further understood that data and determined medical diagnoses, conditions and/or events may be used to improve and/or further train the one or more algorithms. As shown in setting 314 of FIG. 3, user device may indicate that the "Self Exam" is "Complete" and may present a button on a user interface to display the results. User device 302 may display the results (e.g., hypertension detected) on the screen of user device 302.

Figure 4:
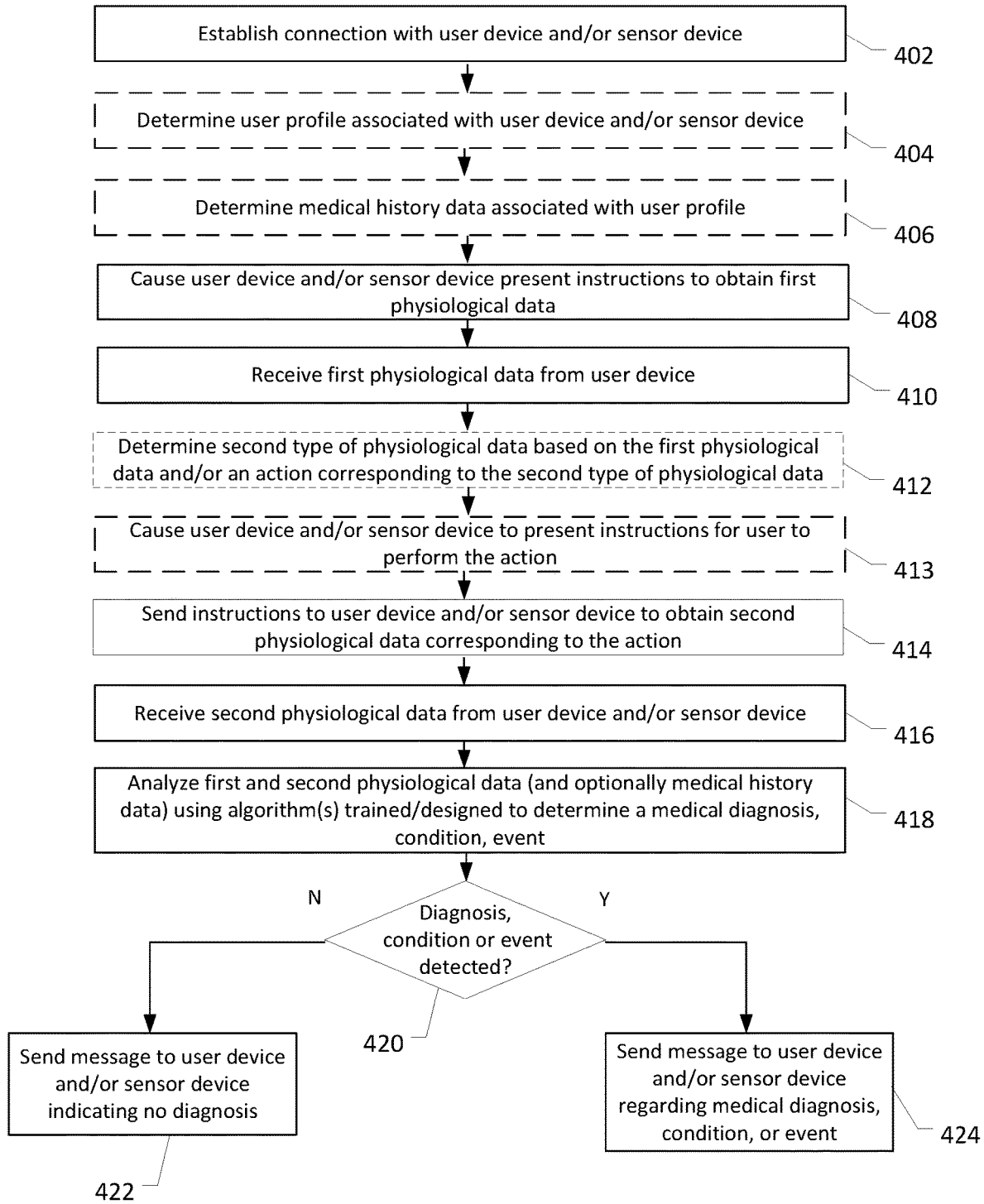
FIG. 4 illustrates an exemplary process flow for guided self-examination for determining a medical diagnosis.

Referring now to FIG. 4, an example process flow for determining a medical diagnosis, condition or event, in accordance with one or more example embodiments of the present disclosure is illustrated. Some or all of the blocks of the process flows in this disclosure may be performed in a distributed manner across any number of devices (e.g., computing devices, user devices, and/or servers). Some or all of the operations of the process flow may be optional and may be performed by different computing devices.

At block 402, computer-executable instructions stored on a memory of a device, such as a computing device, may be executed to establish a connection with a user device (e.g., smart phone) and/or sensor device (e.g., smart watch) associated with a user profile. At optional block 404, computer-executable instructions stored on a memory of a device, such as a computing device, may be executed to determine a user profile associated with the user device and/or sensor device. At optional block 406, computer-executable instructions stored on a memory of a device, such as a computing device, may be executed to determine medical history data associated with the user profile (e.g., medical information about the individual that is the subject of the user profile). The medical history data may be optionally decrypted at block 406. For example, the medical history data received may be encrypted using any well-known encryption techniques (e.g., well-known asymmetric, symmetric and/or blockchain encryption techniques).

At block 408, computer-executable instructions stored on a memory of a device, such as a computing device, may be executed to cause the user device and/or sensor device to present instructions to obtain first physiological data (e.g., any physiological or other data or information relating to a user's body, body function, body characteristics, body measurements, body properties, and the like). At block 410, computer-executable instructions stored on a memory of a device, such as a computing device, may be executed to receive first physiological data (e.g., image of face) from the user device. The first physiological data may be optionally decrypted at block 406. For example, the first physiological data received may be encrypted using any well-known encryption techniques (e.g., well-known asymmetric, symmetric and/or blockchain encryption techniques).

At optional block 412, computer-executable instructions stored on a memory of a device, such as a computing device, may be executed to determine, based on the first physiological data, a second type of physiological data that would be helpful for determining a medical diagnosis, condition, and/or event. This determination may be based on and/or informed by devices associated with the user profile determined at block 404. At optional block 413, computer-executable instructions stored on a memory of a device, such as a computing device, may be executed to cause the user device and/or sensor device to present instructions for the user to perform an action (e.g., exercise, take a deep breath, lie down, etc.).

At block 414, computer-executable instructions stored on a memory of a device, such as a computing device, may be executed to send instructions to the user device and/or sensor device to obtain second physiological data corresponding to the action. The second physiological data may be associated with the second type of physiological data and/or a device known to generate the second type of physiological data. Alternatively, the user device and/or sensor device may automatically obtain such data.

At block 416, computer-executable instructions stored on a memory of a device, such as a computing device, may be executed to receive second physiological data (e.g., heart rate data) from the user device and/or sensor device. The second physiological data may be optionally decrypted at block 406. For example, the second physiological data received may be encrypted using any well-known encryption techniques (e.g., well-known asymmetric, symmetric and/or blockchain encryption techniques). At block 418, computer-executable instructions stored on a memory of a device, such as a computing device, may be executed to analyze first and second physiological data and optionally medical history data) using one or more algorithms trained and/or designed to detect a medical diagnosis, condition or event based on the received data. Detecting a medical diagnosis, condition or event may include determining the likelihood or risk of a medical diagnosis, condition or event.

At decision 420, computer-executable instructions stored on a memory of a device, such as a computing device, may be executed to determine if a medical diagnosis, condition, or event has been detected. If no diagnosis, condition, or event was detected, at block 422, computer-executable instructions stored on a memory of a device, such as a computing device, may be executed to send a message to the user device and/or sensor device indicating that there has been no diagnosis, condition, or event detected. Alternatively, if a diagnosis, condition, or event was detected, at block 424 computer-executable instructions stored on a memory of a device, such as a computing device, may be executed to send a message to the user device regarding the detected medical diagnosis, condition or event. Information about the medical diagnosis, condition, and/or emergency may be optionally encrypted at block 424 using any well-known encryption techniques (e.g., well-known asymmetric, symmetric and/or blockchain encryption techniques).

Figure 5:
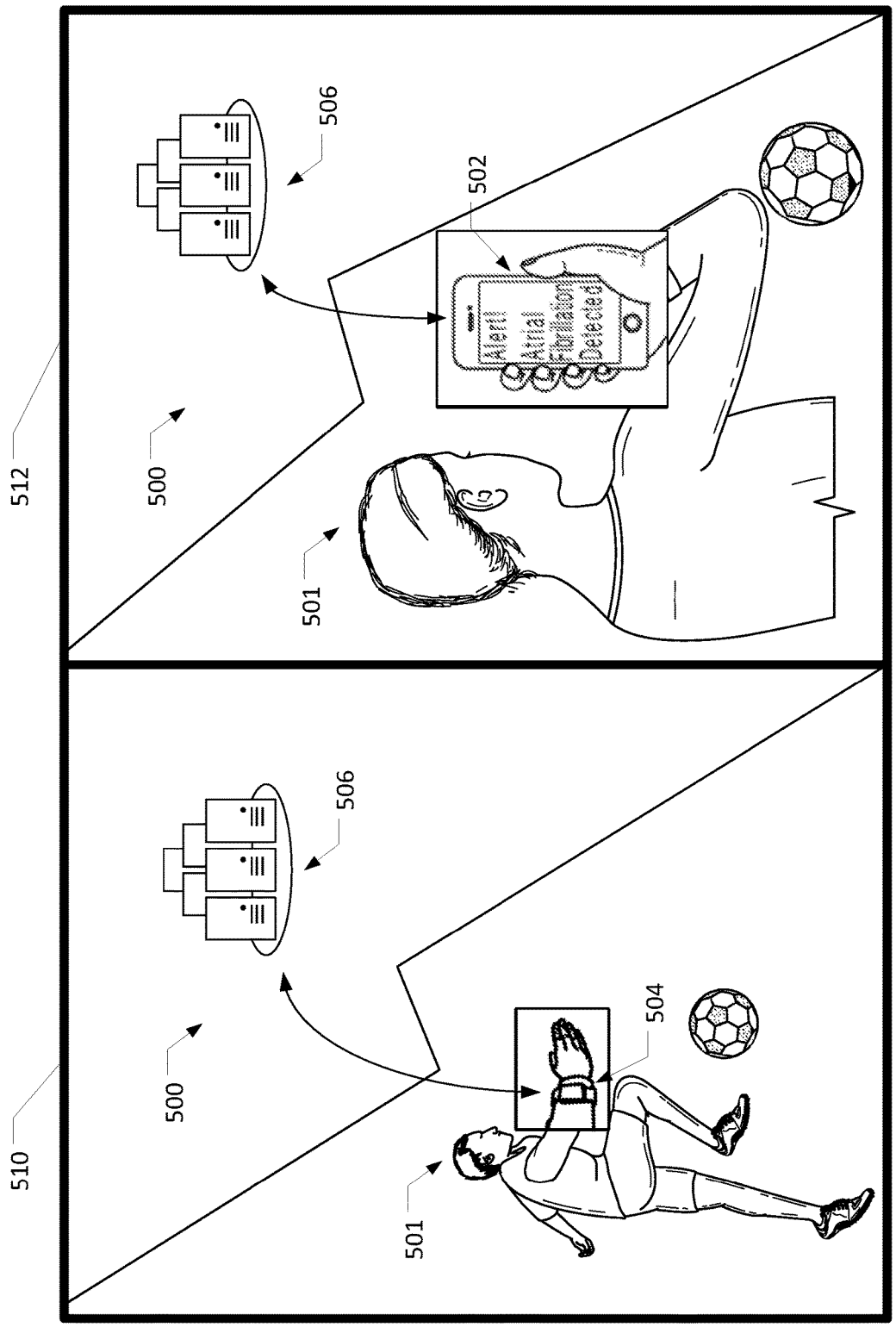
FIG. 5 illustrates an exemplary automated diagnosis system including biometric authentication.

Referring now to FIG. 5, an exemplary biometric authentication and monitoring system is illustrated. Biometric authentication and monitoring system 500 may include user device 502, sensor device 504, and/or computing device 506. User device 502 may be the same as user device 302. Further, sensor device 504 and computing device 506 may be the same as or similar to smart device 104 and computing device 102 described above with respect to FIG. 1, respectively. It is understood that additional or fewer devices (e.g., connected devices) than those shown in FIG. 5 may be included in biometric authentication and monitoring system 500. In an alternative arrangement, computing device 506 may be a local device.

As shown in FIG. 5, biometric authentication and monitoring system 500 may continuously monitor a user. To confirm that the user wearing sensor device 504 is the user corresponding to a user profile, computing device 506 may perform biometric authentication using biometric data obtained by sensor device 504. In the example shown in setting 510, user 301 may wear sensor device 504 (e.g., a smart watch) that may continuously generate biometric data (e.g., any data including a biological or physiological measurement or other information that may be used to identify an individual) and send biometric data to computing device 506. In this manner, a user may be active (e.g., may be playing a sport) and sensor device 504 may collect biometric and/or physiological data while the user is active. It is understood that any other well-known recognition or authentication technique and/or system may be alternatively or additionally employed to authenticate the individual.

As shown in setting 512, computing device 506 may analyze the biometric and/or physiological data received from sensor device 504 and/or any other biometric, physiological, or other relevant data received from other connected devices and/or computing devices (e.g., medical history) and may determine if a medical diagnosis, condition or event is detected (e.g., using one or more algorithms trained to detect a diagnosis, condition or event). It is further understood that data and determined medical diagnoses, conditions and/or events may be used to improve and/or further train the one or more algorithms. Biometric authentication and monitoring system 500 may cause user device 502 to present a message that such diagnosis, condition or event was detected (e.g., atrial fibrillation detected) and may include additional information about the medical diagnosis, condition or event. For example, user device 502 may present treatment recommendations.

Figure 6:
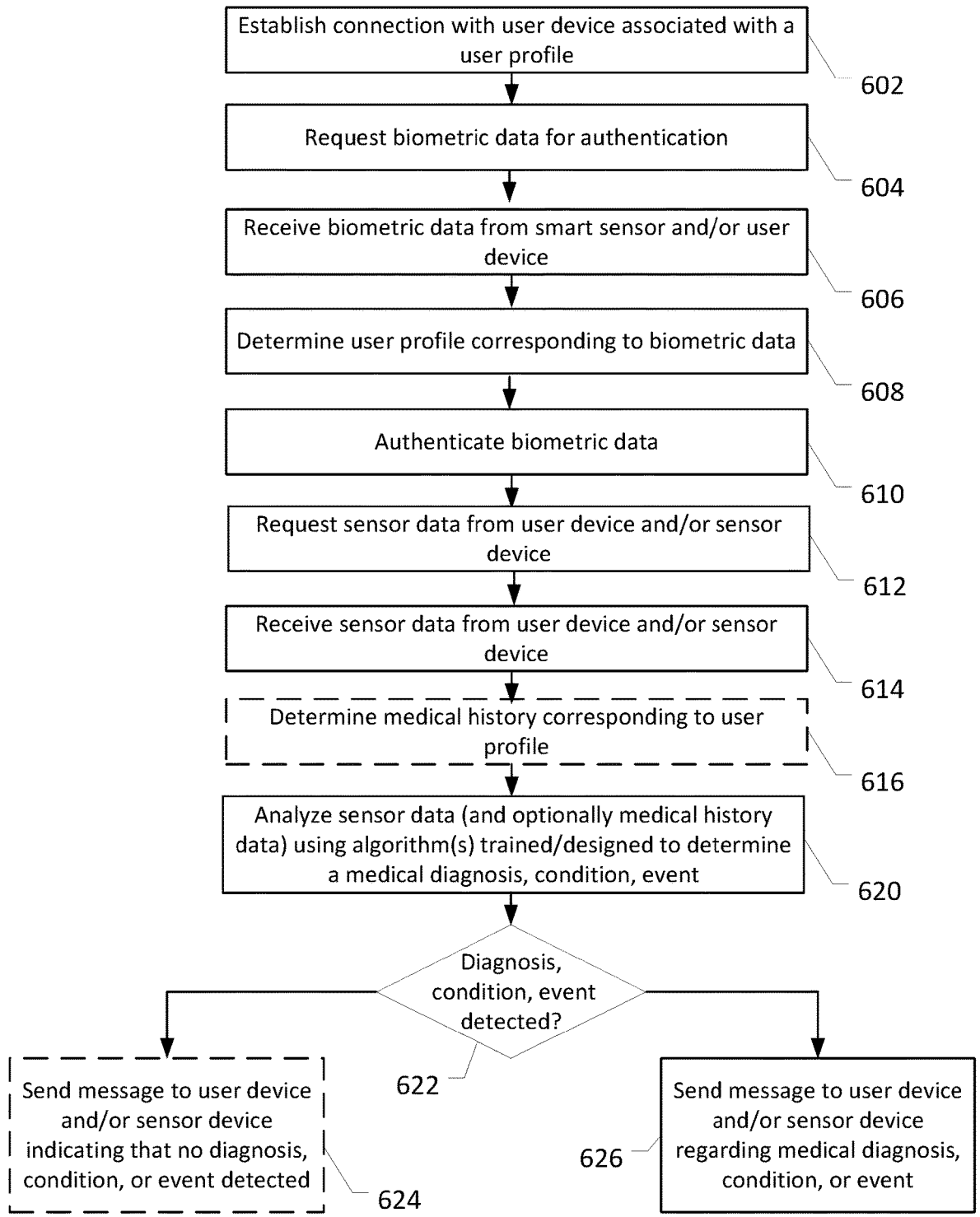
FIG. 6 illustrates an exemplary process flow for biometric authentication and automated diagnosis.

Referring now to FIG. 6, an example process flow for performing biometric authentication and monitoring, in accordance with one or more example embodiments of the present disclosure is illustrated. Some or all of the blocks of the process flows in this disclosure may be performed in a distributed manner across any number of devices (e.g., computing devices, user devices, and/or servers). Some or all of the operations of the process flow may be optional and may be performed in a different order and/or by different computing devices.

At block 602, computer-executable instructions stored on a memory of a device, such as a computing device, may be executed to establish a connection with a user device associated with a user profile. At block 604, computer-executable instructions stored on a memory of a device, may be executed to request biometric data for authentication from the user device. At block 606, computer-executable instructions stored on a memory of a device, may be executed to receive biometric data form the user device, or optionally an associated sensor device, in response to request for biometric data. The biometric data may be optionally decrypted at block 606. For example, the biometric data received may be encrypted using any well-known encryption techniques (e.g., well-known asymmetric, symmetric and/or blockchain encryption techniques).

At block 608, computer-executable instructions stored on a memory of a device, such as a computing device, may be executed to determine a user profile corresponding to the biometric data. For example, the user may send credentials (e.g., username and passcode) to computing device and computing device may use this information to determine a corresponding user profile. Alternatively, or additionally, an identification value associated with the user device may be communicated to the computing device and associated with a user profile.

At block 610, computer-executable instructions stored on a memory of a device, such as a computing device, may be executed to authenticate the biometric data received from the user device. For example, one or more algorithms on computing device may analyze the biometric data and determine that it matches biometric data associated with the user profile. A match may be an exact match or a likelihood or similarity (e.g., that satisfies a threshold value). At block 612, computer-executable instructions stored on a memory of a device, such as a computing device, may be executed to request sensor data from the sensor device and/or user device (e.g., physiological data). Alternatively, the sensor device and/or user device may be preprogrammed to continuously or periodically send sensor data to the computing device once the user has been authenticated.

At block 614, computer-executable instructions stored on a memory of a device, such as a computing device, may be executed to receive sensor data from the user device and/or sensor device. The sensor data may be optionally decrypted at block 614. For example, the sensor data received may be encrypted using any well-known encryption techniques (e.g., well-known asymmetric, symmetric and/or blockchain encryption techniques). At optional block 616, computer-executable instructions stored on a memory of a device, such as a computing device, may be executed to determine medical history corresponding to the user profile. At optional block 618, computer-executable instructions stored on a memory of a device, such as a computing device, may be executed to determine medical history corresponding to the user profile.

At block 620, computer-executable instructions stored on a memory of a device, such as a computing device, may be executed to analyze sensor data and, optionally medical history data, using one or more algorithms trained and/or designed to determine a medical diagnosis, condition or event based on the received data. At decision 622, computer-executable instructions stored on a memory of a device, such as a computing device, may be executed to determine if a medical diagnosis, condition, or event has been detected.

If no diagnosis, condition, or event was detected, at block 624, computer-executable instructions stored on a memory of a device, such as a computing device, may be executed to send a message to the user device and/or sensor device indicating that there has been no diagnosis, condition, or event was detected. Alternatively, if a diagnosis, condition, or event was detected, at block 626 computer-executable instructions stored on a memory of a device, such as a computing device, may be executed to send a message to the user device regarding the detected medical diagnosis, condition or event. This message may include a recommended treatment (e.g., elevate legs). Information about the medical diagnosis, condition, and/or emergency may be optionally encrypted at block 626 using any well-known encryption techniques (e.g., well-known asymmetric, symmetric and/or blockchain encryption techniques).

Figure 7:
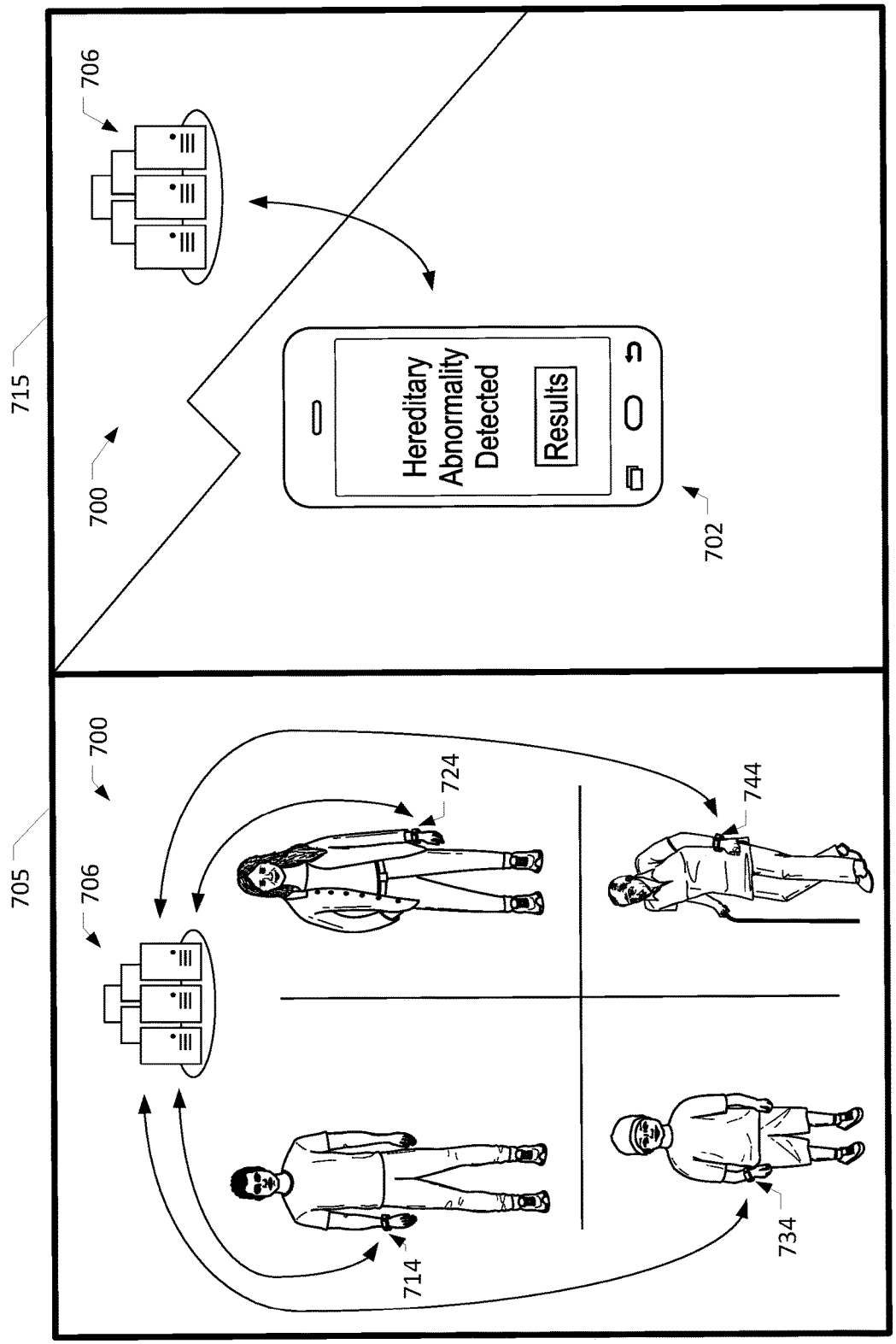
FIG. 7 illustrates a hereditary medical diagnostic system.

Referring now to FIG. 7, an exemplary hereditary monitoring system is illustrated. Hereditary monitoring system 700 may include multiple sensor devices, one or more user devices (e.g., user device 702), and computing device 706. For example, sensor device 714 may be worn by a first user, sensor device 724 may be worn by a second user (e.g., a sister of the first user), sensor device 734 may be worn by a third user (e.g., a child of the first user), and user device 744 may be worn by a fourth user (e.g., a father of the first user), and each of the first user, second user, third user, and fourth user may be related by blood. It is understood that additional or fewer devices (e.g., connected devices) than those shown in FIG. 7 may be included in hereditary monitoring system 700. In an alternative arrangement, computing device 706 may be a local device.

Each of the sensor device 714, sensor device 724, sensor device 734, and sensor device 744 may be the same as or similar to sensor device 104 and computing device 706 may be the same as or similar to computing device 102 described above with respect to FIG. 1. Each of sensor device 714, sensor device 724, sensor device 734, and sensor device 744 may correspond to a family user profile and, as shown in setting 705, may obtain sensor data and send sensor data to computing device 706. For example, computing device 706 may request sensor data and/or each sensor device may be programmed to continuously and/or periodically send sensor data to computing device 706.

As shown in setting 715, computing device 706 may analyze (e.g., using one or more algorithms) the sensor data (e.g., physiological data) received from sensor device sensor device 714, sensor device 724, sensor device 734, and sensor device 744 and/or any other physiological or other relevant data received from other connected devices and/or computing devices (e.g., medical history of each user associated with the family user profile) and a medical diagnosis or condition may be detected from such data. It is further understood that data and determined medical diagnoses, conditions and/or events may be used to improve and/or further train the one or more algorithms. Computing device 706 may cause one or more user device associated with the family user profile (e.g., user device 702) to present a message that such diagnosis or condition was detected (e.g., hereditary abnormality detected) and may include additional information about the medical diagnosis or condition. While four sensor devices and users are illustrated, it is understood that any number of users and/or any type of connected devices may be used in hereditary monitoring system 700.

Figure 8:
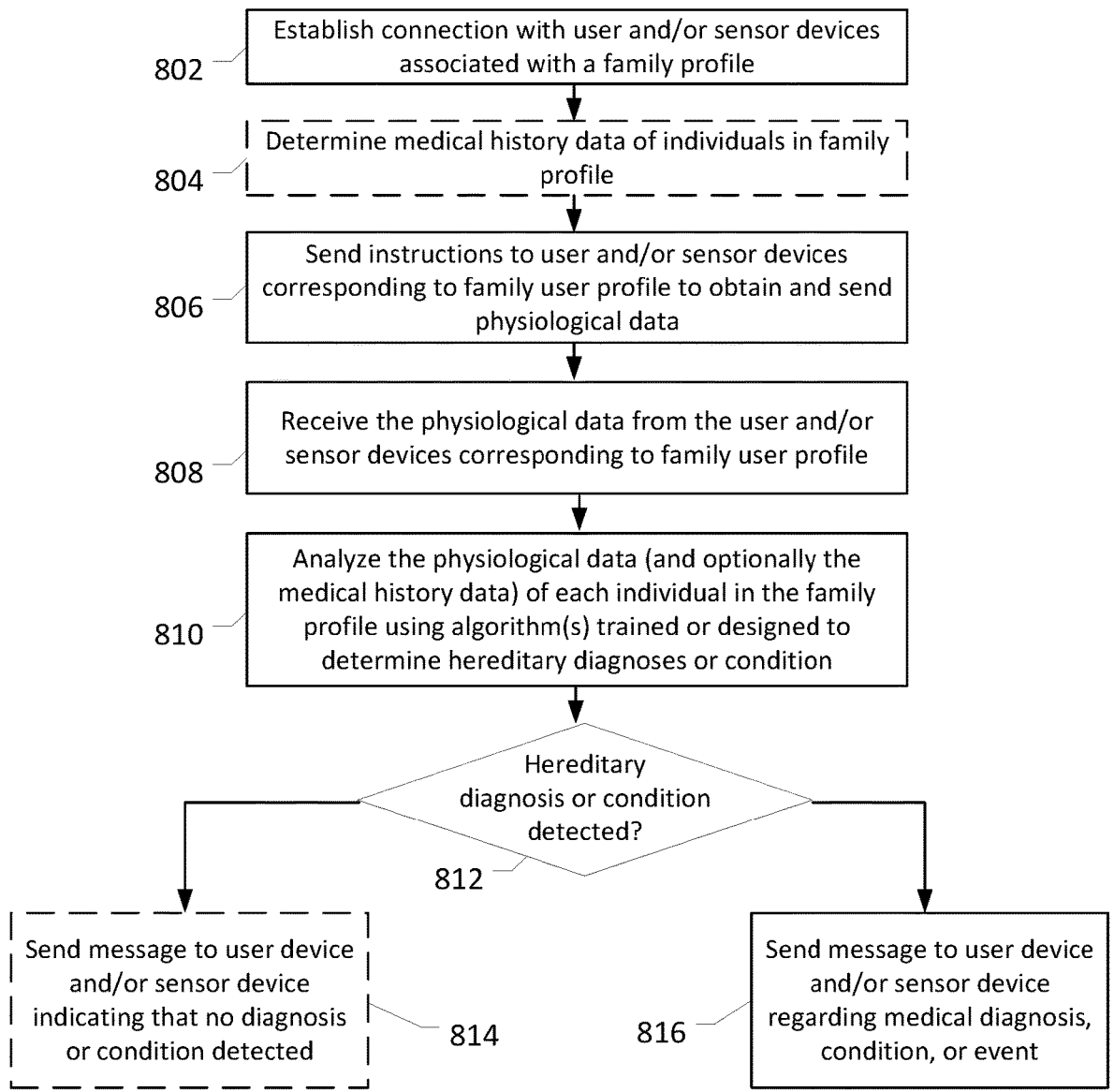
FIG. 8 illustrates an exemplary process flow for a hereditary medical diagnostic system.

Referring now to FIG. 8, an example process flow for hereditary monitoring is illustrated, in accordance with one or more example embodiments of the present disclosure. Some or all of the blocks of the process flows in this disclosure may be performed in a distributed manner across any number of devices (e.g., computing devices user devices, and/or servers). Some or all of the operations of the process flow may be optional and may be performed in a different order and/or by different computing devices.

At block 802, computer-executable instructions stored on a memory of a device, such as a computing device, may be executed to establish a connection with user devices and/or sensor devices, or other connected devices, associated with a family user profile associated with individuals that are related to one another by blood. At optional block 804, computer-executable instructions stored on a memory of a device, may be executed to determine medical history data relevant to one or more individuals in the family user profile. The medical history data may be optionally decrypted at block 804. For example, the medical history data received may be encrypted using any well-known encryption techniques (e.g., well-known asymmetric, symmetric and/or blockchain encryption techniques). At block 806, computer-executable instructions stored on a memory of a device, such as a computing device, may be executed to send instructions to user and/or sensor devices corresponding to family user profile to obtain and send physiological data.

At block 808, computer-executable instructions stored on a memory of a device, such as a computing device, may be executed to receive the physiological data from the user and/or sensor devices corresponding to the family user profile. The physiological data may be optionally decrypted at block 808. For example, the physiological data received may be encrypted using any well-known encryption techniques (e.g., well-known asymmetric, symmetric and/or blockchain encryption techniques). At block 810, computer-executable instructions stored on a memory of a device, such as a computing device, may be executed to analyze the physiological data, and optionally the medical history data, of each individual in the family user profile using one or more algorithms trained and/or designed to determine hereditary diagnoses or conditions.

At decision 812, computer-executable instructions stored on a memory of a device, such as a computing device, may be executed to determine if a medical diagnosis or condition has been detected. If no hereditary diagnosis or condition was detected, at optional block 814, computer-executable instructions stored on a memory of a device, such as a computing device, may be executed to send a message to one or more user device and/or sensor device in the family user profile, indicating that there has been no hereditary diagnosis or condition detected. The system may continue to receive biometric data and/or medical history data (e.g., regarding treatments) and if data subsequently collected is indicative of a hereditary diagnosis or condition, block 816 may be initiated.

If a hereditary diagnosis or condition was detected, at block 816 computer-executable instructions stored on a memory of a device, such as a computing device, may be executed to send a message to one or more user device and/or sensor device regarding the detected hereditary diagnosis or condition, which may include information about the diagnosis or condition. Information about the medical diagnosis, condition, and/or emergency may be optionally encrypted at block 816 using any well-known encryption techniques (e.g., well-known asymmetric, symmetric and/or blockchain encryption techniques).

Figure 9:
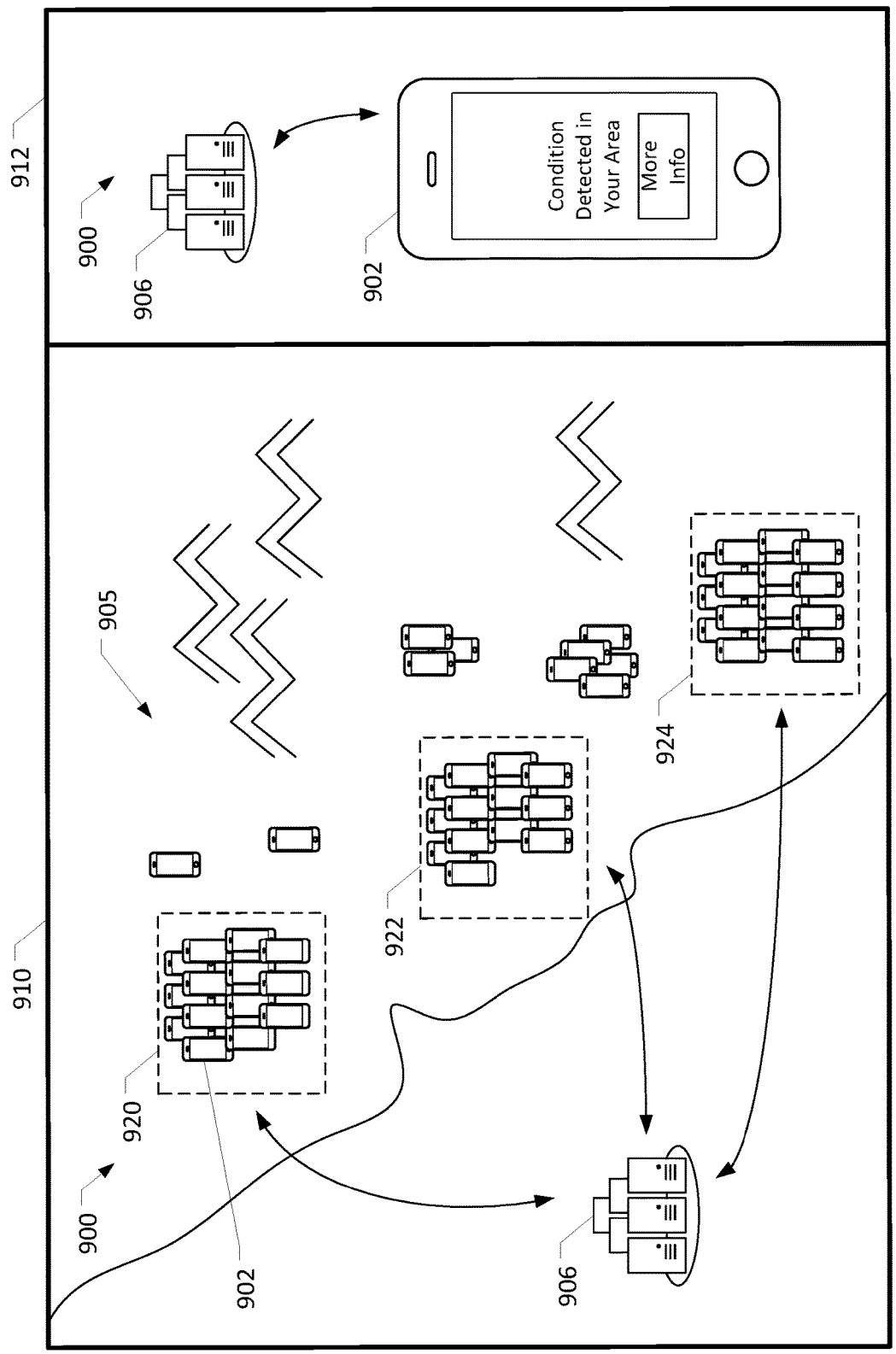
FIG. 9 illustrates an area-based medical diagnostic system.

Referring now to FIG. 9, an exemplary area-based monitoring system is illustrated. Area-based monitoring system 900 may include several user devices (e.g., user device 902) that may be distributed across a region, such as region 905. User devices, such as user device 902, may be the same as or similar to user device 302 described above with respect to FIG. 3. Computing device 906 may be the same as or similar to computing device 102 described above with respect to FIG. 1. Area-based monitoring system 900 may further include several other connected devices such as sensor devices. It is understood that the user devices (e.g., user device 902) and any other connected devices may communicate with computing device 906. It is understood that additional or fewer devices (e.g., connected devices) than those shown in FIG. 9 may be included in area-based monitoring system 900.

As shown in setting 910 of FIG. 9, area-based monitoring system 900 may include connected devices (e.g., user device 902) that are grouped into certain areas or regions based on proximity to one another (e.g., based on geolocation of a user device). For example, connected devices may be grouped into area 920, area 922 and area 924. Connected devices in areas 920, 922 and 924 may continuously and/or periodically send physiological data to computing device 906. Computing device 906 may optionally have access to medical history data corresponding to the users of the connected devices. Computing device 906 may analyze the physiological data and/or other relevant data received from each area and may compare such data from different areas to determine if there is high rate or risk of a medical diagnosis or condition in one area as compared to other areas.

As shown in setting 912, if computing device 906 determines a high rate or risk of a medical diagnosis or condition in one area as compared to other areas, computing device 906 may send a connected device, such as user device 902, a message regarding the medical diagnosis or condition. The device may present the message including a button or link for more information.

Figure 10:
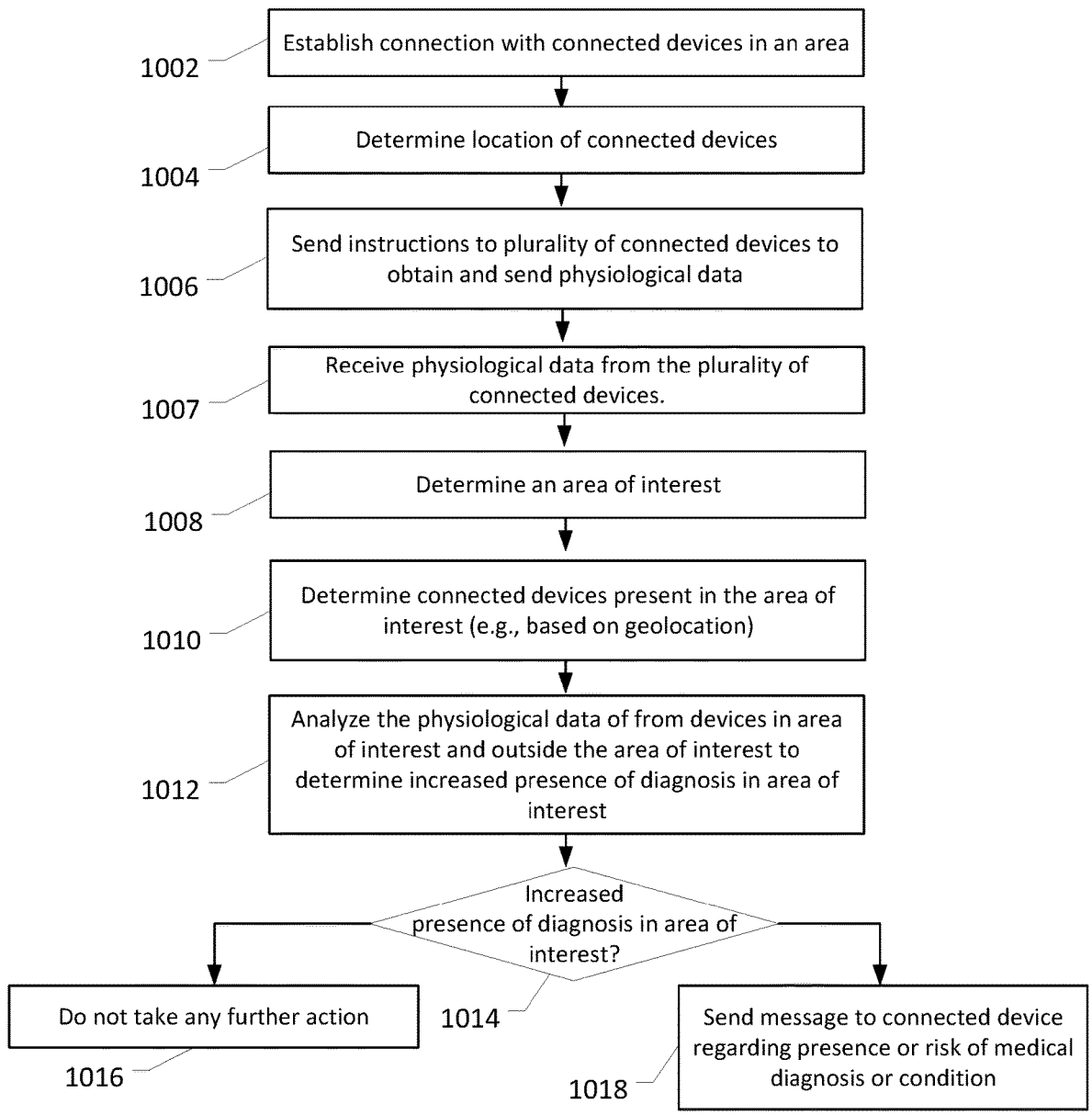
FIG. 10 illustrates an exemplary process flow for an area-based medical diagnostic system.

Referring now to FIG. 10, an example process flow for area-based monitoring is illustrated, in accordance with one or more example embodiments of the present disclosure. Some or all of the blocks of the process flows in this disclosure may be performed in a distributed manner across any number of devices (e.g., computing devices, user devices, and/or servers). Some or all of the operations of the process flow may be optional and may be performed in a different order and/or by different computing devices.

At block 1002, computer-executable instructions stored on a memory of a device, such as a computing device, may be executed to establish a connection with a plurality of connected devices (e.g., user device and/or sensor device). At block 1004, computer-executable instructions stored on a memory of a device, such as a computing device, may be executed to determine the location of the connected devices (e.g., geolocation). At block 1006, computer-executable instructions stored on a memory of a device, such as a computing device, may be executed to send instructions to the connected devices to obtain and send physiological data. Alternatively, or additionally, the connected devices may be programmed to continuously or periodically send physiological data to the computing device.

At block 1006, computer-executable instructions stored on a memory of a device, such as a computing device, may be executed to receive the physiological data from the plurality of connected devices. The physiological data may be optionally decrypted at block 1007. For example, the physiological data received may be encrypted using any well-known encryption techniques (e.g., well-known asymmetric, symmetric and/or blockchain encryption techniques).

At block 1008, computer-executable instructions stored on a memory of a device, such as a computing device, may be executed to determine an area of interest (e.g., within a certain radius). For example, computing device may group devices within a certain radius (e.g., 50 miles) into a single "area." At block 1010, computer-executable instructions stored on a memory of a device, such as a computing device, may be executed to determine connected devices present in the area of interest (e.g., based on geolocation).

At block 1012, computer-executable instructions stored on a memory of a device, such as a computing device, may be executed to determine analyze the physiological data from devices in area of interest and outside the area of interest to determine increased presence or risk of a medical diagnosis or condition in the area of interest. For example, one or more algorithms designed and/or trained to determine the presence or risk of a medical diagnosis or condition may be employed.

At decision 1014, computer-executable instructions stored on a memory of a device, such as a computing device, may be executed to determine if an increased presence or risk of a medical diagnosis or condition has been detected in the area of interest, as compared to the presence or risk outside of the area of interest. If no increased presence or risk of a diagnosis or condition is detected, at block 1016, no action may be performed. Alternatively, if an increased presence or risk of a diagnosis or condition is detected, at block 1018 computer-executable instructions stored on a memory of a device, such as a computing device, may be executed to send a message to the user device regarding the increased presence or risk of a medical diagnosis or condition. Information about the risk of a diagnosis or condition may be optionally encrypted at block 1018 using any well-known encryption techniques (e.g., well-known asymmetric, symmetric and/or blockchain encryption techniques).

Figure 11:
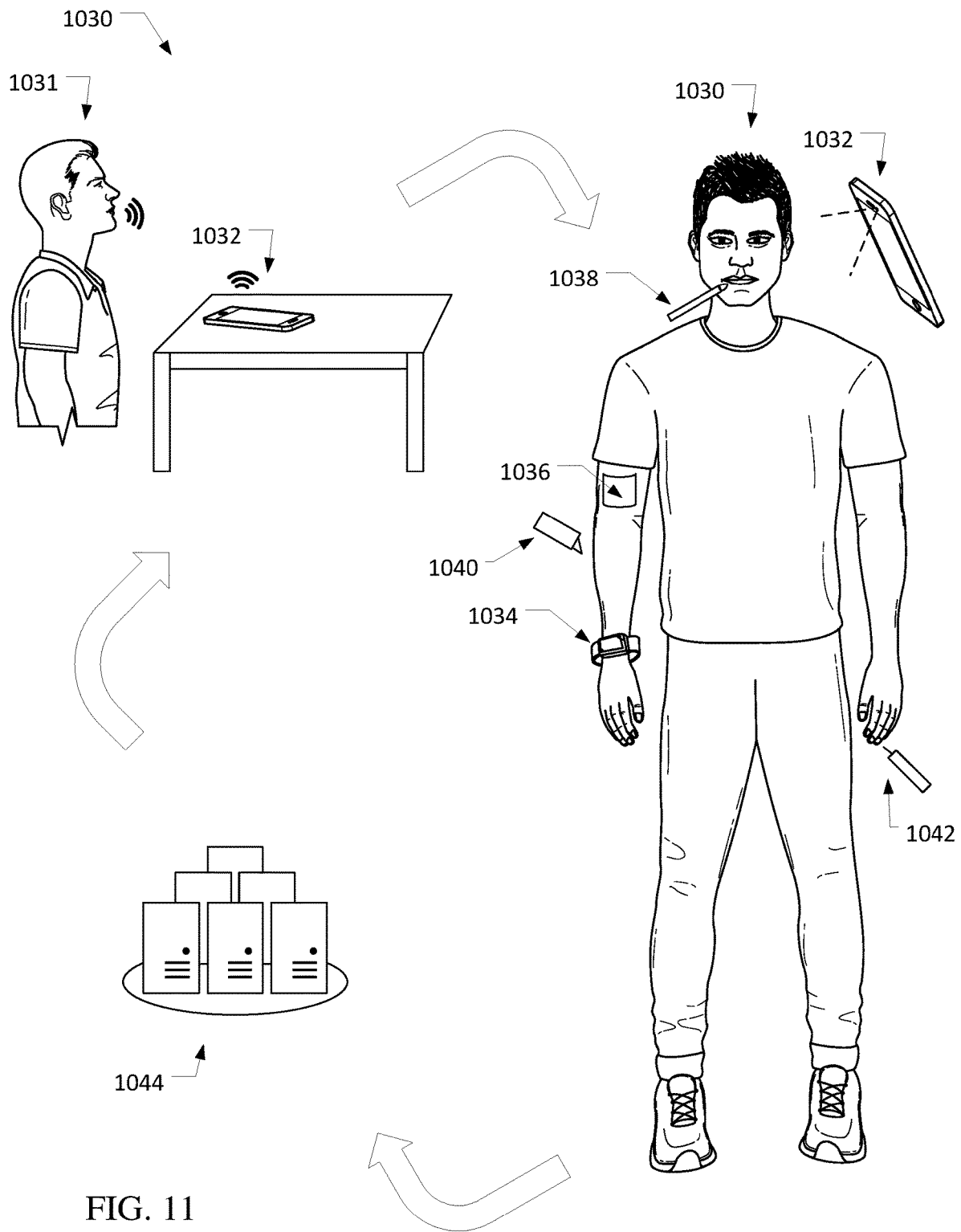
FIG. 11 illustrates an exemplary medical diagnostic system.

Referring now to FIG. 11, an exemplary diagnostic system is illustrated in accordance with the present disclosure. Diagnostic system 1030 may include user device 1032, sensor device 1034, patch device 1036, saliva device 1038, tissue device 1040, blood device 1042 and/or computing device 1044, which may be a remote computing device. Sensor device 1034 and computing device 1044 may be the same as or similar to sensor device 104 and computing device 102, respectively, described above with respect to FIG. 1. Sensor device 1034 may be a wearable device (e.g., smart watch) and/or may include one or more photoplethysmography (PPG) sensors and/or accelerometers. User device 1032 may be the same or similar to user device 302 described above with respect to FIG. 3.

Patch device 1036 may be a device worn by a user that may detect blood pressure, heart rate, ECG, and/or any other physiological information. In one example, patch device 1036 may be an adhesive or elastic band with a one or more sensors designed to detect blood pressure, heart rate, ECG, and/or any other related information, a microprocessor, a transceiver and a power unit. Tissue device 1040 may be a device that may collect a tissue sample (e.g., superficial skin sample) and may analyze the tissue sample using one or more sensors. In one example, tissue device 1040 may be a standalone device or alternatively may be incorporated into another device (e.g., patch 1036). The tissue device 1040 may include one or more sensors designed to generate data and/or a signal corresponding to the tissue sample, a microprocessor, a transceiver and a power unit. Blood device 1042 may be a device that may collect blood and may analyze the blood sample using one or more sensors. In one example, blood device 1042 may be standalone device or alternatively may be incorporated into another device (e.g., patch 1036). The blood device 1042 may include one or more sensors designed to generate data and/or a signal corresponding to the blood sample, a microprocessor, a transceiver and a power unit. Saliva device 1038 may be a device that may collect saliva and may analyze the saliva sample using one or more sensors. In one example, saliva device 1038 may be standalone device. Saliva device 1038 may include one or more sensors designed to generate data and/or a signal corresponding to the saliva sample, a microprocessor, a transceiver and a power unit. Alternatively, or in addition, a similar device designed to generate data and/or a signal corresponding to a bodily secretion sample (e.g., sweat) may be employed.

User device 1032 may communicate with computing device 1044 via any well-known wired or wireless system (e.g., Wi-Fi, cellular network, Bluetooth, Bluetooth Low Energy (BLE), near field communication protocol, etc.). Additionally, user device may communicate with sensor device 1034, patch device 1036, saliva device 1038, tissue device 1040, blood device 1042 and/or computing device 1044 via any well-known wired or wireless system. It is understood that sensor device 1034, patch device 1036, saliva device 1038, tissue device 1040, and/or blood device 1042 may communicate with computer device 1044 via user device 1032 and/or may communicate with computing device 1044 directly (e.g., via any well-known wireless system).

As shown in FIG. 11, user 1031 may be close in proximity to user device 1032 such that user 1031 may view a display on user device 1032 and/or hear audio presented on user device 1032. User 1031 may use the user device 1032 in a home, office, restaurant and/or outdoors for example. User 1031 may use diagnostic system 1030 for a preventative check-up and/or when suffering from symptoms.

As shown in FIG. 11, user device 1032 may present audio information requesting certain medical information from user 1031. For example, user device 1032 may request that user 1031 explain, via spoken words, the type of symptoms the user is experiencing (e.g., cough, fever, aches, runny nose, etc.). User device 1032 may send data indicative of the spoken words to computing device 1044 to transcribe the spoken words and/or determine the meaning of the spoken words (e.g., using well-known voice recognition and/or processing systems). Alternatively, user device 1032 may perform this function.

Computing device 1044 may analyze the spoken words to determine one or more types of data that would be relevant determining a medical condition, diagnosis, and/or event relevant to the spoken words (i.e., symptoms information). For example, computing device 1044 may analyze the spoken words using one or more trained algorithms (e.g. neural networks) to make this determination. Computing device 1044 may send instructions to user device 1032 to request more information from user 1031 based on the symptoms input already analyzed. Alternatively, or additionally, user device 1032 may ask user 1031 to type out the symptoms and/or medical information on the phone and the typed information may be sent to computing device 1044 for processing in the same manner.

Based on the symptoms and/or other information collected by user device 1032 and communicated to computing device 1044, computing device 1044 may determine that certain types of data and/or medical information must be collected about the user. For example, sensor device 1034, patch device 1036, saliva device 1038, tissue device 1040, and/or blood device 1042 may be in communication with user device 1032 and/or computing device 1044 and/or computing device 1044 may know which devices are available to collect information.

Computing device 1044 may determine that data from sensor device 1034 and/or patch device 1036, saliva device 1038, tissue device 1040, and blood device 1042 is desirable for making a determination regarding the medical diagnosis, condition and/or event. Computing device may request data from sensor device 1034 and/or patch device 1036, such as blood pressure data, heart rate data and/or other circulatory related information. It is understood that one or more of sensor device 1034 and patch device 1036 may be used. Sensor device 1034 and/or patch device 1036 may send the data determined and/or generated by sensor device 1034 and/or patch device 1036 (e.g., blood pressure, heart rate and/or ECG data) to computing device 1044 and/or user device 1032.

Computing device 1044 may additionally, or alternatively, request data from user device 1032. For example, user device 1032 may include a high definition and/or high resolution camera for capturing high definition images of the user's body. In one example the user device 1032 may be coupled to a scope or other imaging component for capturing images in or around a body orifice (e.g., mouth, ear, etc.). A user may position the user device 1032 such that an image may be captured at the appropriate location of the user's body. User device 1032 may send the data determined and/or generated by user device 1032 (e.g., high definition and/or high resolution image data) to computing device 1044. The image may be processed by the computing device 1044 and/or user device 1032 for diagnostic purposes and/or to track changes of a body part over time (e.g., modification of a nevus into a melanoma).

Computing device 1044 may additionally, or alternatively, request data from saliva device 1038. For example, the user may position saliva device 1038 in the user's mouth to collect a sample of saliva that may be detected and/or processed by saliva device 1038. Saliva device 1038 may send the data determined and/or generated by saliva device 1038 (e.g., saliva data) to computing device 1044 and/or user device 1032. It is understood that this data may be used by computing device 1044 for genetic testing, for example.

Computing device 1044 may additionally, or alternatively, request data from tissue device 1040. For example, the user may position tissue device 1040 at a certain location on the user's body (e.g., on the user's arm) to collect a sample of tissue (e.g., a superficial skin sample) that may be detected and/or processed by tissue device 1040. Tissue device 1040 may send the data (e.g., tissue data) determined and/or generated by tissue device 1040 to computing device 1044 and/or user device 1032.

Computing device 1044 may additionally, or alternatively, request data from blood device 1042. For example, the user may position blood device 1042 at a certain location on the user's body (e.g., on the tip of the user's finger) to collect a sample of blood that may be detected and/or processed by blood device 1042. Blood device 1042 may send the data (e.g., blood data) determined and/or generated by blood device 1042 to computing device 1044 and/or user device 1032. The blood data may be used for biological dosage purposes, for example.

Computing device 1044 may additionally, or alternatively, request data motion data from sensor device 1034. For example, the sensor device may determine motion data using one or more accelerometers. Sensor device 1034 may send the data (e.g., motion data) determined and/or generated by sensor device 1034 to computing device 1044 and/or user device 1032. The motion data may be indicative of a position of the user (e.g., supine) and/or a gait of a user, for example.

Computing device 1044 may analyze the data determined and/or generated by sensor device 1034, patch device 1036, saliva device 1038, tissue device 1040, blood device 1042, and/or user device 1032 and may analyze the data and the symptoms using one or more algorithms trained and/or designed to detect a medical diagnosis, condition or event based on the received data. For example, the computing device 1044 may determine the likelihood or risk of a medical diagnosis, condition or event. It is further understood that data and determined medical diagnoses, conditions and/or events may be used to improve and/or further train the one or more algorithms. It is understood that a fewer or greater number of devices than those illustrated in FIG. 11 may be used and/or different devices than those illustrated in FIG. 11 may be employed.

If a diagnosis, condition, or event was detected, or a high risk of the foregoing is detected (e.g., above a threshold) a message may be sent to the user device to be presented by the user device to inform the user of the detected medical diagnosis, condition or event or risk thereof. Such information may be optionally using any well-known encryption techniques. It is understood that one or more of the operations of computing device 1044 described above with respect to FIG. 11 may be performed by user device 1032.

In one example, all of the operations of computing device 1044 described herein may be performed by user device 1032.

Figure 12:
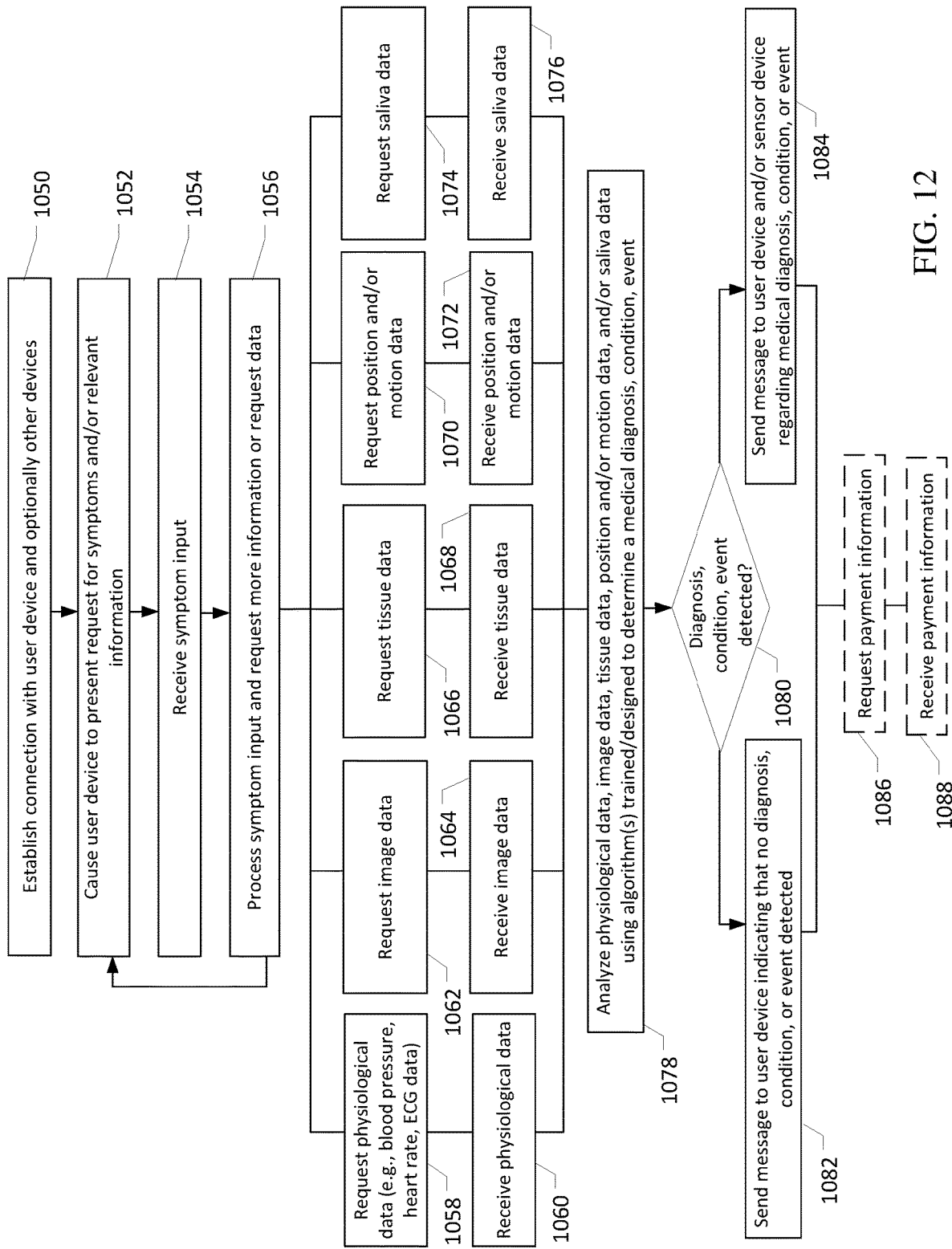
FIG. 12 illustrates an exemplary process flow for the medical diagnostic system.

Referring now to FIG. 12, an example process flow for determining a medical diagnosis, condition or event using a medical diagnostic system, in accordance with one or more example embodiments of the present disclosure is illustrated. Some or all of the blocks of the process flows in this disclosure may be performed in a distributed manner across any number of devices (e.g., computing devices, user devices, and/or servers). Some or all of the operations of the process flow may be optional and may be performed by different computing devices.

At block 1050, computer-executable instructions stored on a memory of a device, such as a computing device, may be executed to establish a connection with a user device (e.g., smart phone or kiosk) and optionally one or more sensor device (e.g., smart watch), patch device, tissue device, saliva device, blood device, and/or any other device. At block 1052, computer-executable instructions stored on a memory of a device, such as a computing device, may be executed cause the user device to present a request for symptoms and/or other relevant medical information. For example, the user device may audibly ask the user to explain the symptoms and/or medical issue. Alternatively, or additionally, the user device may present this request on a display of the user device and the user may type in their response or speak their response.

At block 1054, computer-executable instructions stored on a memory of a device, such as a computing device, may be executed to receive the symptom input (e.g., from spoken words and/or text) which may be indicative of the symptoms the patient is experiencing. The user device may include well-known voice recognition and processing software to transcribe and/or determine the meaning of the spoken words. The information and/or data received at block 1054 may be optionally decrypted at block 1054. For example, the data received may be encrypted (e.g., by the user device) using any well-known encryption techniques (e.g., well-known asymmetric, symmetric and/or blockchain encryption techniques).

At block 1056, computer-executable instructions stored on a memory of a device, such as a computing device, may be executed to process the symptom input (e.g., using one or more algorithms and/or neural networks). The computing device may determine that more information is required about the symptoms and/or other relevant information is needed and thus block 1052 may be reinitiated. Additionally, or alternatively, the computing device may use the information received at block 1054 to determine request one or more types of data from one or more devices. The devices and data types may depend on the symptoms input received at block 1054.

The computing device may send request for data corresponding to the user either to the user device, which may relay such request to the appropriate device, or may send such request directly to the appropriate device. It is understood that one or more of blocks 1058, 1062, 1066, 1070 and/or 1074 may be optional and/or that data other than the data illustrated in FIG. 12 may be requested (e.g., other body secretion data). It is further understood that blocks 1058, 1062, 1066, 1070 and/or 1074 may be performed simultaneously or in any other order.

At block 1058, computer-executable instructions stored on a memory of a device, such as a computing device, may be executed to request physiological data (e.g., blood pressure data, heart rate data and/or ECG data) from one or more devices and/or the user device may present instructions to the user to obtain such data using the appropriate device. For example, such data may be requested from a sensor device and/or a patch device (e.g., via the user device). At block 1060, computer-executable instructions stored on a memory of a device, such as a computing device, may be executed to receive physiological data (e.g., from the user device and/or from other devices). The physiological data may be optionally decrypted at block 1060. For example, the physiological data received may be encrypted (e.g., by the user device) using any well-known encryption techniques (e.g., well-known asymmetric, symmetric and/or blockchain encryption techniques) and may need to be decrypted.

At block 1062, computer-executable instructions stored on a memory of a device, such as a computing device, may be executed to request image data from one or more devices and/or the user device may present instructions to the user to obtain such data using the appropriate device. For example, such data may be requested from a user device and/or a camera device. At block 1064, computer-executable instructions stored on a memory of a device, such as a computing device, may be executed to receive image data (e.g., indicative of a portion of the user's body and/or an orifice). The image data may be optionally decrypted at block 1064. For example, the image data received may be encrypted (e.g., by the user device) using any well-known encryption techniques (e.g., well-known asymmetric, symmetric and/or blockchain encryption techniques) and may need to be decrypted.

At block 1066, computer-executable instructions stored on a memory of a device, such as a computing device, may be executed to request tissue data (e.g., based on a skin tissue sample) from one or more devices and/or the user device may present instructions to the user to obtain such data using the appropriate device. For example, such data may be requested from a tissue device. At block 1068, computer-executable instructions stored on a memory of a device, such as a computing device, may be executed to receive tissue data. The tissue data may be optionally decrypted at block 1068. For example, the tissue data received may be encrypted (e.g., by the user device) using any well-known encryption techniques (e.g., well-known asymmetric, symmetric and/or blockchain encryption techniques) and may need to be decrypted.

At block 1070, computer-executable instructions stored on a memory of a device, such as a computing device, may be executed to request position and/or motion data from one or more devices and/or the user device may present instructions to the user to obtain such data using the appropriate device. The position and/or motion data may be indicative of a user's position and/or gait, for example. In one example, such data may be requested from a sensor device having one or more accelerometers. At block 1072, computer-executable instructions stored on a memory of a device, such as a computing device, may be executed to receive motion and/or position data. The motion and/or position data may be optionally decrypted at block 1072. For example, the motion data received may be encrypted (e.g., by the user device) using any well-known encryption techniques (e.g., well-known asymmetric, symmetric and/or blockchain encryption techniques) and may need to be decrypted.

At block 1074, computer-executable instructions stored on a memory of a device, such as a computing device, may be executed to request saliva data from one or more devices and/or the user device may present instructions to the user to obtain such data using the appropriate device. In one example, such data may be requested from a saliva device.

At block 1076, computer-executable instructions stored on a memory of a device, such as a computing device, may be executed to receive saliva data. The saliva data may be optionally decrypted at block 1076. For example, the saliva data received may be encrypted (e.g., by the user device) using any well-known encryption techniques (e.g., well-known asymmetric, symmetric and/or blockchain encryption techniques) and may need to be decrypted.

At block 1078, computer-executable instructions stored on a memory of a device, such as a computing device, may be executed to analyze the physiologic data, image data, tissue data, position and/or motion data, and/or saliva data, and optionally the symptom input received at block 1054, using one or more algorithms trained and/or designed to detect a medical diagnosis, condition or event based on such data. Detecting a medical diagnosis, condition or event may include determining the likelihood or risk of a medical diagnosis, condition or event.

At decision 1080, computer-executable instructions stored on a memory of a device, such as a computing device, may be executed to determine if a medical diagnosis, condition, or event has been detected. If no diagnosis, condition, or event was detected, at block 1082, computer-executable instructions stored on a memory of a device, such as a computing device, may be executed to send a message to the user device indicating that there has been no diagnosis, condition, or event detected. This message may cause the user device to present (e.g., visually and/or audibly) that no diagnosis, condition or event was detected. Alternatively, if a diagnosis, condition, or event was detected, at block 1084 computer-executable instructions stored on a memory of a device, such as a computing device, may be executed to send a message to the user device regarding the detected medical diagnosis, condition or event. This message may cause the user device to present (e.g., visually and/or audibly) the diagnosis, condition or event that was detected. Information about the medical diagnosis, condition, and/or emergency may be optionally encrypted at block 1084 using any well-known encryption techniques (e.g., well-known asymmetric, symmetric and/or blockchain encryption techniques).

At optional block 1086, computer-executable instructions stored on a memory of a device, such as a computing device, may be executed to request payment information from the user device. At optional block 1088, computer-executable instructions stored on a memory of a device, such as a computing device, may be executed to receive payment information from the user device. It is understood that blockchain technology may be used to facilitate and/or secure the payment transaction using well-known blockchain techniques.

Figure 13:
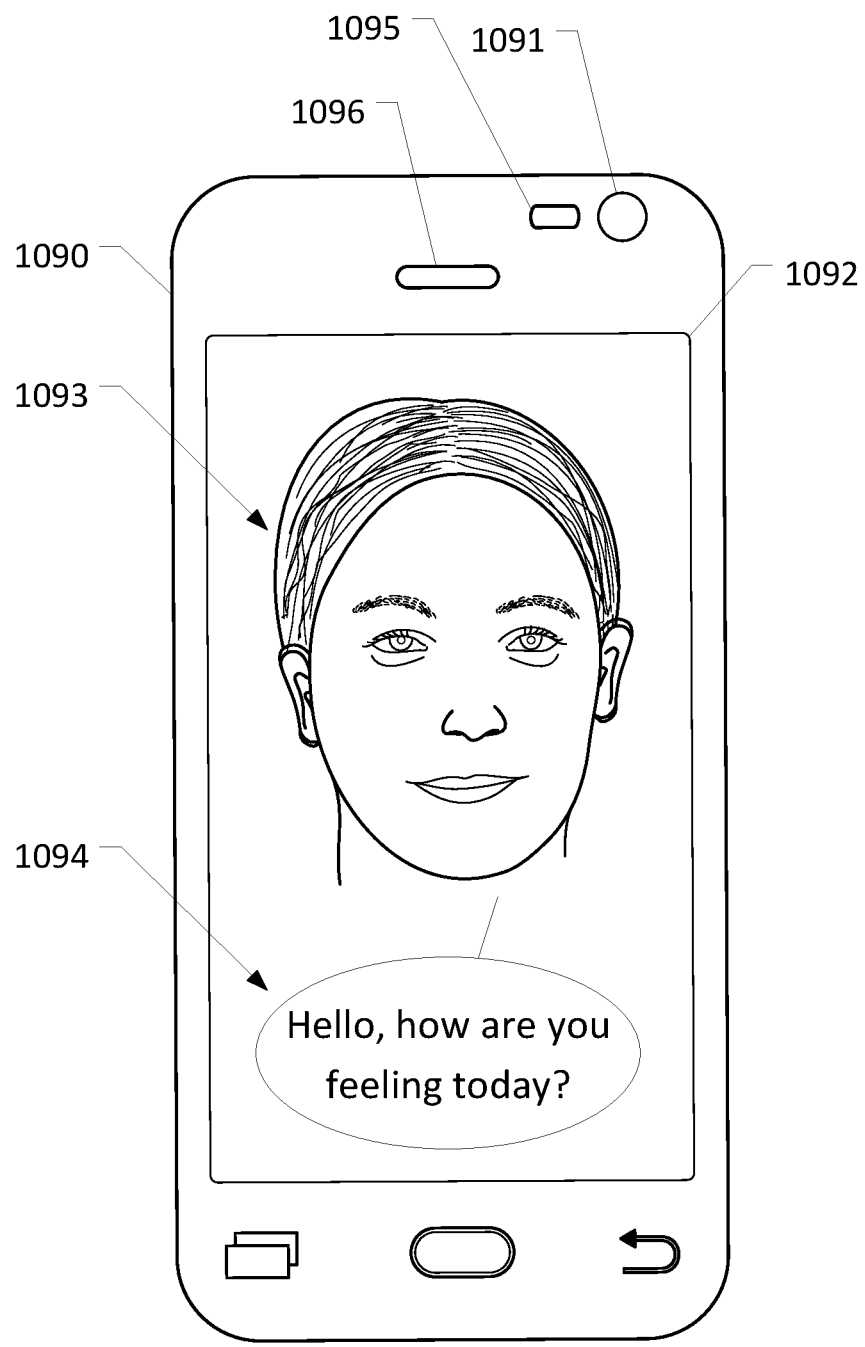
FIG. 13 illustrates an exemplary user interface including an avatar for communicating with a user.

Referring now to FIG. 13 an exemplary user interface including an avatar for communicating with a user is illustrated in accordance with one or more example embodiments of the disclosure. As shown in FIG. 13, user device 1090, which may be the same as or similar to user device 302 described above with respect to FIG. 3, may be used by a user to communicate with a medical diagnostic system described herein (e.g., the medical diagnostic system described above with respect to FIG. 12). User device 1090 may include microphone 1095, camera 1091, speaker 1096 and display 1092.

As shown in FIG. 13, user device 1090 may generate, and display 1092 may visually present, avatar 1093 which may be a human-like image (e.g., face) that may move and appear to speak. For example, avatar 1093 may have lips that move with words that are audibly presented by speaker 1096, such that avatar 1093 appears to speak the words. Avatar 1093 may move its eyes and head, or other body feature as applicable, to appear more human-like. Avatar 1093 may be controlled by user device 1092 and/or a server, which may be similar to or the same as server 102 running a medical diagnostic system.

Avatar 1093 may be used to interact with the user to cause the user to provide user input with respect to symptoms and other health related information. The input received from the user (e.g., audio data) may be processed and/or transcribed by the user device and/or the server (e.g., such input may be sent from user device 1090 to the server). User device 1090 may present the spoken words of the avatar on speaker 1096 and/or may cause corresponding text to be presented on display 1092 (e.g., using text bubble 1094).

The user device and/or server may include logic (e.g., software algorithms and/or trained machine learning models) that analyze the user input and generate follow-up questions to elicit additional information that may be more accurate and/or more in-depth. For example, avatar 1093 may say "hello, how are you feeling today" and the user may say "not well, my head hurts." Upon processing this user input, the avatar and user device 1090 may be caused to ask the user where their head hurts. For example, Avatar 1093 may be used to request symptom and/or other relevant information at steps 1052 and 1056 described above with respect to FIG. 12.

It is understood that the more human-like interaction for the user as compared to solely audio instructions presented by user device 1090 may be less stressful and/or more comfortable for the user. As a result, a user may be more likely to disclose information in this fashion and thus may provide more accurate and in depth responses. As an added benefit, the human-like interaction with the avatar may be therapeutic for some users as it may be reassuring that their concerns and ailments are being listened to and addressed.

Figure 14:
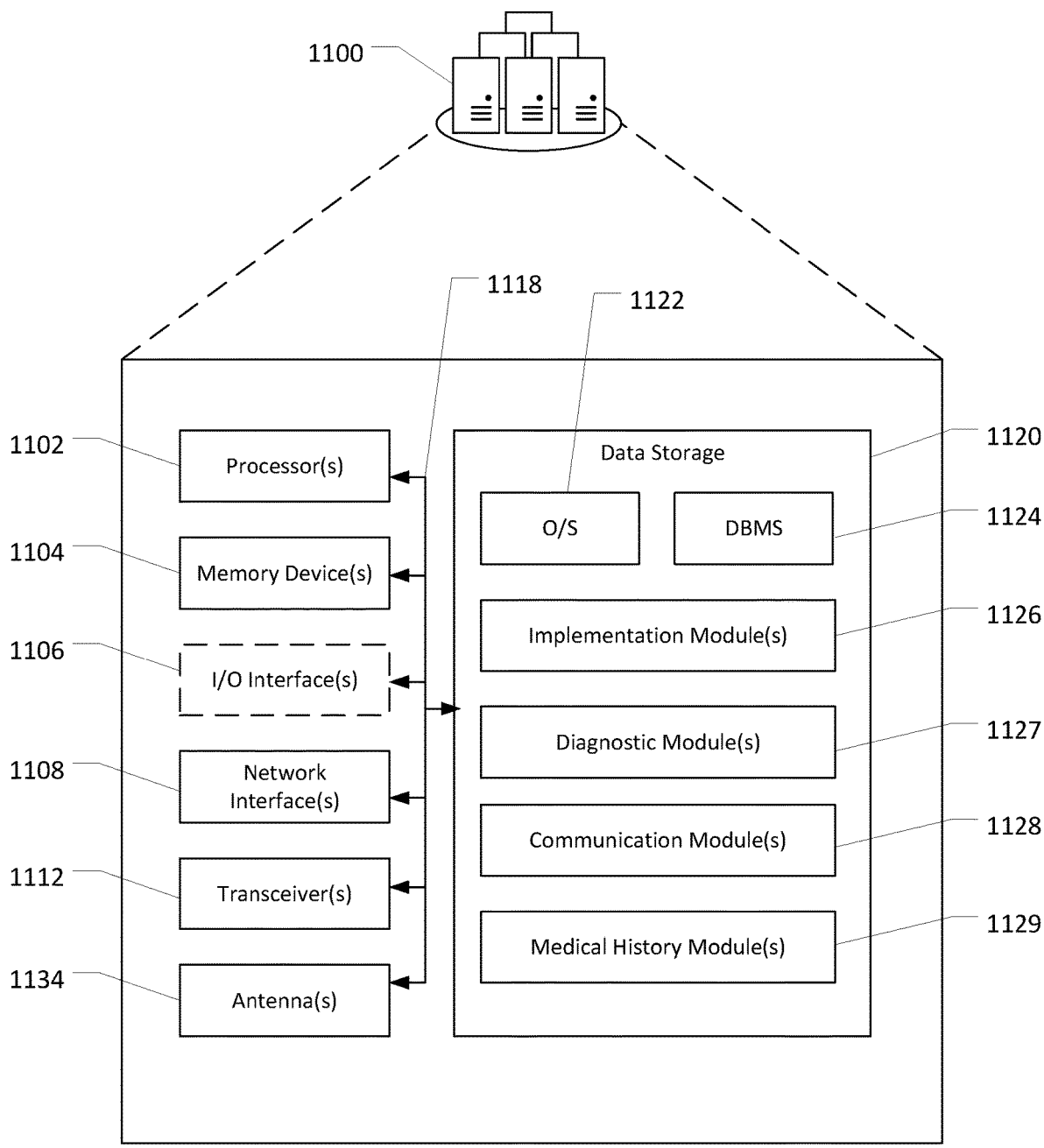
FIG. 14 is a schematic block diagram of a computing device, in accordance with one or more example embodiments of the disclosure.

Referring now to FIG. 14 a schematic block diagram of computing device 1100 is illustrated in accordance with one or more example embodiments of the disclosure. Computing device 1100 may be one or more computing devices and/or servers and may include any suitable computing device capable of receiving and/or sending data, and may optionally be coupled to connected devices including, but not limited to, smart phones, smart devices, sensor devices, wearable devices, computing devices, tablets, smart television, smart sensor, or any other well-known user device, and/or one or more servers, datastores, or the like. Computing device 1100 may correspond to an illustrative device configuration for any computing device of FIGS. 1-13 and/or any computing devices running a medical monitoring and/or diagnostic system described herein. For example, computing device 1100 may be the same as computing device 102 of FIG. 1.

Computing device 1100 may be configured to communicate via one or more networks with one or more connected devices or the like. Example network(s) may include, but are not limited to, any one or more different types of communications networks such as, for example, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. Further, such network(s) may have any suitable communication range associated therewith and may include, for example, global networks (e.g., the Internet), metropolitan area networks (MANs), wide area networks (WANs), local area networks (LANs), or personal area networks (PANs). In addition, such network(s) may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

In an illustrative configuration, the computing device 1100 may include one or more processors (processor(s)) 1102, one or more memory devices 1104 (generically referred to herein as memory 1104), one or more of the optional input/output (I/O) interface(s) 1106, one or more network interface(s) 1108, one or more transceivers 1112, and one or more antenna(s) 1134. The computing device 1100 may further include one or more buses 1118 that functionally couple various components of the computing device 1100. The computing device 1100 may further include one or more antenna(e) 1134 that may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals including BLE signals, a Near Field Communication (NFC) antenna for transmitting or receiving NFC signals, a 900 MHz antenna, and so forth. These various components will be described in more detail hereinafter.

The bus(es) 1118 may include at least one of a system bus, a memory bus, an address bus, or a message bus, and may permit exchange of information (e.g., data (including computer-executable code), signaling, etc.) between various components of the computing device 1100. The bus(es) 1118 may include, without limitation, a memory bus or a memory controller, a peripheral bus, an accelerated graphics port, and so forth. The bus(es) 1118 may be associated with any suitable bus architecture including, without limitation, an Industry Standard Architecture (ISA), a Micro Channel Architecture (MCA), an Enhanced ISA (EISA), a Video Electronics Standards Association (VESA) architecture, an Accelerated Graphics Port (AGP) architecture, a Peripheral Component Interconnects (PCI) architecture, a PCI-Express architecture, a Personal Computer Memory Card International Association (PCMCIA) architecture, a Universal Serial Bus (USB) architecture, and so forth.

The memory 1104 of the computing device 1100 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 1104 may include multiple different types of memory such as various types of static random access memory (SRAM), various types of dynamic random access memory (DRAM), various types of unalterable ROM, and/or writeable variants of ROM such as electrically erasable programmable read-only memory (EEPROM), flash memory, and so forth. The memory 904 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage 1120 may include removable storage and/or non-removable storage including, but not limited to, magnetic storage, optical disk storage, and/or tape storage. The data storage 1120 may provide non-volatile storage of computer-executable instructions and other data. The memory 1104 and the data storage 1120, removable and/or non-removable, are examples of computer-readable storage media (CRSM) as that term is used herein.

The data storage 1120 may store computer-executable code, instructions, or the like that may be loadable into the memory 904 and executable by the processor(s) 1102 to cause the processor(s) 1102 to perform or initiate various operations. The data storage 1120 may additionally store data that may be copied to memory 1104 for use by the processor(s) 1102 during the execution of the computer-executable instructions. Moreover, output data generated as a result of execution of the computer-executable instructions by the processor(s) 1102 may be stored initially in memory 1104, and may ultimately be copied to data storage 1120 for non-volatile storage.

More specifically, the data storage 1120 may store one or more operating systems (O/S) 1122; one or more database management systems (DBMS) 1124; and one or more program module(s), applications, engines, computer-executable code, scripts, or the like such as, for example, one or more implementation module(s) 1126, one or more diagnostic module(s) 1127, one or more communication module(s) 1128, and/or one or more medical history modules(s) 1129. Some or all of these module(s) may be sub-module(s). Sub or all of these module(s) may be part of the product platform and some or all of these modules may be part of the synthetic platform. Any of the components depicted as being stored in data storage 1120 may include any combination of software, firmware, and/or hardware. The software and/or firmware may include computer-executable code, instructions, or the like that may be loaded into the memory 904 for execution by one or more of the processor(s) 1102. Any of the components depicted as being stored in data storage 1120 may support functionality described in reference to correspondingly named components earlier in this disclosure.

The data storage 1120 may further store various types of data utilized by components of the computing device 1100. Any data stored in the data storage 1120 may be loaded into the memory 1104 for use by the processor(s) 1102 in executing computer-executable code. In addition, any data depicted as being stored in the data storage 1120 may potentially be stored in one or more datastore(s) and may be accessed via the DBMS 1124 and loaded in the memory 1104 for use by the processor(s) 1102 in executing computer-executable code. The datastore(s) may include, but are not limited to, databases (e.g., relational, object-oriented, etc.), file systems, flat files, distributed datastores in which data is stored on more than one node of a computer network, peer-to-peer network datastores, or the like. In FIG. 14, the datastore(s) may include, for example, user preference information, user contact data, device pairing information, and other information.

The processor(s) 1102 may be configured to access the memory 1104 and execute computer-executable instructions loaded therein. For example, the processor(s) 1102 may be configured to execute computer-executable instructions of the various program module(s), applications, engines, or the like of the computing device 1100 to cause or facilitate various operations to be performed in accordance with one or more embodiments of the disclosure. The processor(s) 1102 may include any suitable processing unit capable of accepting data as input, processing the input data in accordance with stored computer-executable instructions, and generating output data. The processor(s) 1102 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), an application-specific integrated circuit, a digital signal processor (DSP), and so forth. Further, the processor(s) 1102 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 1102 may be capable of supporting any of a variety of instruction sets.

Referring now to functionality supported by the various program module(s) depicted in FIG. 14, the implementation module(s) 1126 may include computer-executable instructions, code, or the like that responsive to execution by one or more of the processor(s) 1102 may perform functions including, but not limited to, overseeing coordination and interaction between one or more modules and computer executable instructions in data storage 1120 and/or determining user selected actions and tasks. Implementation module 1126 may further coordinate with communication module 1128 to send messages to connected devices and receive messages from the computing device.

The diagnostic module(s) 1128 may include computer-executable instructions, code, or the like that responsive to execution by one or more of the processor(s) 1102 may perform functions including, but not limited to, analyzing data received from connected devices such a visual data, audio data, physiological data, and any other type of data. Diagnostic module 1128 may further analyze other information such as medical device history. Diagnostic module 1128 may run one or more algorithms that may be train models or neural networks designed to determine a medical diagnosis, condition and/or event.

The communication module(s) 1128 may include computer-executable instructions, code, or the like that responsive to execution by one or more of the processor(s) 1102 may perform functions including, but not limited to, communicating with one or more computing devices, for example, via wired or wireless communication, communicating with connected devices, communicating with one or more servers (e.g., remote servers), communicating with remote datastores and/or databases, sending or receiving notifications or commands/directives, communicating with cache memory data, and the like.

The medical history module(s) 1129 may include computer-executable instructions, code, or the like that responsive to execution by one or more of the processor(s) 802 may perform functions including, but not limited to storing and/or maintaining data and/or information corresponding to medical history data and any other user related data.

Referring now to other illustrative components depicted as being stored in the data storage 1120, the O/S 1122 may be loaded from the data storage 1120 into the memory 1104 and may provide an interface between other application software executing on the computing device 1100 and hardware resources of the computing device 1100. More specifically, the O/S 1122 may include a set of computer-executable instructions for managing hardware resources of the computing device 1100 and for providing common services to other application programs (e.g., managing memory allocation among various application programs). In certain example embodiments, the O/S 1122 may control execution of the other program module(s) to for content rendering. The O/S 1122 may include any operating system now known or which may be developed in the future including, but not limited to, any server operating system, any mainframe operating system, or any other proprietary or non-proprietary operating system.

The DBMS 1124 may be loaded into the memory 1104 and may support functionality for accessing, retrieving, storing, and/or manipulating data stored in the memory 1104 and/or data stored in the data storage 1120. The DBMS 1124 may use any of a variety of database models (e.g., relational model, object model, etc.) and may support any of a variety of query languages. The DBMS 1124 may access data represented in one or more data schemas and stored in any suitable data repository including, but not limited to, databases (e.g., relational, object-oriented, etc.), file systems, flat files, distributed datastores in which data is stored on more than one node of a computer network, peer-to-peer network datastores, or the like.

Referring now to other illustrative components of the computing device 1100, the optional input/output (I/O) interface(s) 1106 may facilitate the receipt of input information by the computing device 1100 from one or more I/O devices as well as the output of information from the computing device 1100 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the computing device 1100 or may be separate. The I/O devices may further include, for example, any number of peripheral devices such as data storage devices, printing devices, and so forth.

The optional I/O interface(s) 1106 may also include an interface for an external peripheral device connection such as universal serial bus (USB), FireWire, Thunderbolt, Ethernet port or other connection protocol that may connect to one or more networks. The optional I/O interface(s) 1106 may also include a connection to one or more of the antenna(e) 1134 to connect to one or more networks via a wireless local area network (WLAN) (such as Wi-Fi®) radio, Bluetooth, ZigBee, and/or a wireless network radio, such as a radio capable of communication with a wireless communication network such as a Long Term Evolution (LTE) network, WiMAX network, 3G network, ZigBee network, etc.

The computing device 1100 may further include one or more network interface(s) 1108 via which the computing device 1100 may communicate with any of a variety of other systems, platforms, networks, devices, and so forth. The network interface(s) 1108 may enable communication, for example, with one or more wireless routers, one or more host servers, one or more web servers, and the like via one or more of networks.

The antenna(e) 1134 may include any suitable type of antenna depending, for example, on the communications protocols used to transmit or receive signals via the antenna(e) 1134. Non-limiting examples of suitable antennas may include directional antennas, non-directional antennas, dipole antennas, folded dipole antennas, patch antennas, multiple-input multiple-output (MIMO) antennas, or the like. The antenna(e) 1134 may be communicatively coupled to one or more transceivers 1112 or radio components to which or from which signals may be transmitted or received.

As previously described, the antenna(e) 1134 may include a Bluetooth antenna configured to transmit or receive signals in accordance with established standards and protocols, such as Bluetooth and/or BLE. Alternatively, or in addition to, antenna(e) 1134 may include cellular antenna configured to transmit or receive signals in accordance with established standards and protocols, such as or cellular antenna configured to transmit or receive signals in accordance with established standards and protocols, such as Global System for Mobile Communications (GSM), 3G standards (e.g., Universal Mobile Telecommunications System (UMTS), Wideband Code Division Multiple Access (W-CDMA), CDMA2000, etc.), 4G standards (e.g., Long-Term Evolution (LTE), WiMax, etc.), direct satellite communications, or the like. The antenna(e) 1134 may additionally, or alternatively, include a Wi-Fi® antenna configured to transmit or receive signals in accordance with established standards and protocols, such as the IEEE 802.11 family of standards, including via 2.4 GHz channels (e.g., 802.11b, 802.11g, 802.11n), 5 GHz channels (e.g., 802.11n, 802.11ac), or 60 GHz channels (e.g., 802.11ad). In alternative example embodiments, the antenna(e) 1134 may be configured to transmit or receive radio frequency signals within any suitable frequency range forming part of the unlicensed portion of the radio spectrum (e.g., 900 MHz).

The antenna(e) 1134 may additionally, or alternatively, include a GNSS antenna configured to receive GNSS signals from three or more GNSS satellites carrying time-position information to triangulate a position therefrom. Such a GNSS antenna may be configured to receive GNSS signals from any current or planned GNSS such as, for example, the Global Positioning System (GPS), the GLONASS System, the Compass Navigation System, the Galileo System, or the Indian Regional Navigational System.

The transceiver(s) 1112 may include any suitable radio component(s) for—in cooperation with the antenna(e) 1134—transmitting or receiving radio frequency (RF) signals in the bandwidth and/or channels corresponding to the communications protocols utilized by the computing device 1100 to communicate with other devices. The transceiver(s) 1112 may include hardware, software, and/or firmware for modulating, transmitting, or receiving—potentially in cooperation with any of antenna(e) 1134—communications signals according to any of the communications protocols discussed above including, but not limited to, one or more Wi-Fi® and/or Wi-Fi® direct protocols, as standardized by the IEEE 802.11 standards, one or more non-Wi-Fi® protocols, or one or more cellular communications protocols or standards. The transceiver(s) 1112 may further include hardware, firmware, or software for receiving GNSS signals. The transceiver(s) 1112 may include any known receiver and baseband suitable for communicating via the communications protocols utilized by the computing device 1100. The transceiver(s) 1112 may further include a low noise amplifier (LNA), additional signal amplifiers, an analog-to-digital (A/D) converter, one or more buffers, a digital baseband, or the like.

It should be appreciated that the program module(s), applications, computer-executable instructions, code, or the like depicted in FIG. 14 as being stored in the data storage 1120, are merely illustrative and not exhaustive and that processing described as being supported by any particular module may alternatively be distributed across multiple module(s) or performed by a different module. In addition, various program module(s), script(s), plug-in(s), Application Programming Interface(s) (API(s)), or any other suitable computer-executable code hosted locally on the computing device 1100 and/or hosted on other computing device(s) accessible via one or more networks, may be provided to support functionality provided by the program module(s), applications, or computer-executable code depicted in FIG. 14 and/or additional or alternate functionality. Further, functionality may be modularized differently such that processing described as being supported collectively by the collection of program module(s) depicted in FIG. 14 may be performed by a fewer or greater number of module(s), or functionality described as being supported by any particular module may be supported, at least in part, by another module. In addition, program module(s) that support the functionality described herein may form part of one or more applications executable across any number of systems or devices in accordance with any suitable computing model such as, for example, a client-server model, a peer-to-peer model, and so forth. In addition, any of the functionality described as being supported by any of the program module(s) depicted in FIG. 14 may be implemented, at least partially, in hardware and/or firmware across any number of devices.

It should further be appreciated that the computing device 1100 may include alternate and/or additional hardware, software, or firmware components beyond those described or depicted without departing from the scope of the disclosure. More particularly, it should be appreciated that software, firmware, or hardware components depicted as forming part of the computing device 1100 are merely illustrative and that some components may not be present or additional components may be provided in various embodiments. While various illustrative program module(s) have been depicted and described as software module(s) stored in data storage 1120 and/or data storage 1120, it should be appreciated that functionality described as being supported by the program module(s) may be enabled by any combination of hardware, software, and/or firmware. It should further be appreciated that each of the above-mentioned module(s) may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular module may, in various embodiments, be provided at least in part by one or more other module(s). Further, one or more depicted module(s) may not be present in certain embodiments, while in other embodiments, additional module(s) not depicted may be present and may support at least a portion of the described functionality and/or additional functionality. Moreover, while certain module(s) may be depicted and described as sub-module(s) of another module, in certain embodiments, such module(s) may be provided as independent module(s) or as sub-module(s) of other module(s).

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component including assembly language instructions may require conversion into executable machine code by an assembler prior to execution by the hardware architecture and/or platform.

Another example programming language may be a higher-level programming language that may be portable across multiple architectures. A software component including higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component including instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

It should be understood that any of the computer operations described herein above may be implemented at least in part as computer-readable instructions stored on a computer-readable memory. It will of course be understood that the embodiments described herein are illustrative, and components may be arranged, substituted, combined, and designed in a wide variety of different configurations, all of which are contemplated and fall within the scope of this disclosure.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method for determining a medical diagnosis, the method comprising:
   determining a user profile associated with a user device, a first device, a second device, and a third device;
   requesting first data from the first device, the first data corresponding to a first data type;
   receiving the first data from the first device, the first data corresponding to at least a portion of a face of a user and indicative of first symptom data corresponding to a user;
   determining to request additional symptom data based on the first data;
   determining the second device and the third device are configured to generate additional symptom data based on the user profile;
   determining, after determining to request additional symptom data, that a second data type together with the first data type are informative with respect to determining the medical diagnosis;
   determining the second data type is associated with the second device associated with the user profile and not the third device associated with the user profile;

determining to request second data corresponding to the second data type from the second device after determining that the second data type is associated with the second device associated with the user profile and not the third device associated with the user profile;

requesting second data corresponding to the second data type from the second device, the second data indicative of second symptom data;

receiving the second data from the second device;

decrypting one or more of the first data and the second data;

training, using machine learning, at least one algorithm to determine at least one medical diagnosis using at least a plurality of physiological data different than the first data and the second data;

applying the at least one first algorithm trained using machine learning to determine a first medical diagnosis corresponding to the user based on the first data and the second data;

causing the user device to present a message indicating the determined first medical diagnosis;

determining there is a medical emergency corresponding to the first medical diagnosis, wherein determining that there is a medical emergency comprises processing the first data and the second data using at least one second algorithm trained to detect a medical emergency; and sending a second message regarding the medical emergency to one or more of emergency services, wherein the second message sent to one or more emergency services comprises a location corresponding to the user.

2. The method of claim 1, further comprising determining an emergency contact based on the user profile.

3. The method of claim 2, further comprising sending a third message regarding the first medical diagnosis to the emergency contact.

4. The method of claim 3, further comprising encrypting the third message using blockchain prior to sending the third message to the emergency contact.

5. The method of claim 1, further comprising:
requesting third data from a third device associated with the user profile; and
receiving the third data from the third device, the third data indicative of physiological data corresponding to the user; and
wherein the first medical diagnosis is further based on the third data.

6. A computing device for guided medical examination for determining a medical diagnosis, the computing device comprising:
a memory configured to store computer-executable instructions; and
at least one computer processor configured to access the memory and execute the computer-executable instructions to:
establish a connection with a user device, a first sensor device, and a second sensor device, the user device comprising a display and a first sensor, the first sensor device comprising a second sensor, and the second sensor device comprising a third sensor;
determine a user profile associated with at least the user device, the first sensor device, and the second sensor device;
cause the user device to present a request to generate first data using the first sensor, the first data corresponding to a first data type and indicative of first symptom data;
receive the first data from the user device, the first data generated using the first sensor and corresponding to at least a portion of a face of a user;
determine to request additional symptom data based on the first data;
determine the first sensor device and the second sensor device are configured to generate additional symptom data based on the user profile;
determine, after determining to request additional symptom data, that a second data type together with the first data type are informative with respect to determining the medical diagnosis;
determine the second data type is associated with the first sensor device associated with the user profile and not the second sensor device associated with the user profile;
determine to request sensor data corresponding to the second data type from the first sensor device after determining that the second data type is associated with the first sensor device associated with the user profile and not the second sensor device associated with the user profile;
send a request for the sensor data to the first sensor device, the sensor data indicative of second symptom data corresponding to the user;
receive first sensor data from the first sensor device, the first sensor data generated using the second sensor;
decrypt one or more of the first data and the first sensor data;
train, using machine learning, at least one algorithm to determine at least one medical diagnosis using at least a plurality of physiological data different than the first data and the first sensor data;
apply the at least one first algorithm trained using machine learning to determine a first medical diagnosis based on the first data and the first sensor data;
determine there is a medical emergency corresponding to the first medical diagnosis, wherein to determine that there is a medical emergency comprises processing the first data and the second data using at least one second algorithm trained to detect a medical emergency; and
send a message regarding the medical emergency to one or more of emergency services, wherein the message sent to one or more emergency services comprises a location corresponding to the user.

7. The computing device of claim 6, wherein:
the first sensor is a camera, and
the second sensor is a heart rate sensor and the first sensor data is heart rate data corresponding to the user.

8. A method for performing a guided medical examination for determining a medical diagnosis, the method comprising:
establishing a connection with a user device, a first sensor device, and a second sensor device, the user device comprising a display and a first sensor, the first sensor device comprising a second sensor, and the second sensor device comprising a third sensor;
determining a user profile associated with at least the user device, the first sensor device, and the second sensor device;
causing the user device to present a request to generate first data using the first sensor, the first data corresponding to a first data type and indicative of first symptom data;

receiving the first data from the user device, the first data generated using the first sensor and corresponding to at least a portion of a face of a user;
determining to request additional symptom data based on the first data;
determining the first sensor device and the second sensor device are configured to generate additional symptom data based on the user profile;
determining, after determining to request additional symptom data, that a second data type together with the first data type are informative with respect to determining the medical diagnosis;
determining the second data type is associated with the first sensor device and not the second sensor device;
determining to request sensor data corresponding to the second data type from the first sensor device after determining that the second data type is associated with the first sensor device associated with the user profile and not the second sensor device associated with the user profile;
sending, after causing the user device to present instructions for the user to perform the bodily movement, a request for the sensor data to the first sensor device, the sensor data indicative of second symptom data corresponding to the user;
receiving first sensor data from the first sensor device, the first sensor data generated using the second sensor and corresponding to the bodily movement;
decrypting one or more of the first data and the first sensor data;
training, using machine learning, at least one algorithm to determine at least one medical diagnosis using at least a plurality of physiological data different than the first data and the first sensor data;
applying the at least one first algorithm trained using machine learning to determine a first medical diagnosis based on the first data and the first sensor data;
determining there is a medical emergency corresponding to the first medical diagnosis, wherein determining that there is a medical emergency comprises processing the first data and the second data using at least one second algorithm trained to detect a medical emergency; and
sending a message regarding the medical emergency to one or more of emergency services, wherein the message sent to one or more emergency services comprises a location corresponding to the user.

9. The method of claim 8, wherein:
the first sensor is a camera, and
the second sensor is a heart rate sensor and the first sensor data is heart rate data corresponding to the user.

10. A method for determining a medical diagnosis corresponding to a user, the method comprising:
determining a user profile associated with a user device, a first device, a second device, and a third device;
causing a user device to present a request for symptom data using an avatar rendered on a display of the user device;
receiving first symptom data from the user device, the first symptom data corresponding to a first data type;
determining to request additional symptom data based on the first symptom data;
determining the second device and the third device are configured to generate additional symptom data based on the user profile;
determining, after determining to request additional symptom data, that a second data type together with the first data type are informative with respect to determining the medical diagnosis;
determining the second data type is associated with the second device associated with the user profile and not the third device associated with the user profile;
determining to request second symptom data corresponding to the second data type from the second device after determining that the second data type is associated with the second device associated with the user profile and not the third device associated with the user profile;
causing, after determining the second data type associated with the second device, the user device to present a request using the human-like avatar rendered on the display of the user device for the user to perform a bodily movement of one or more of inhaling, exercising, or assuming a bodily position;
requesting, after causing the user device to present the request using the human-like avatar, the second symptom data from the second device, the second symptom data corresponding to the second data type and the bodily movement;
receiving the second symptom data generated by the second device;
decrypting one or more of the first symptom data and the second symptom data;
training, using machine learning, at least one algorithm to determine at least one medical diagnosis using at least a plurality of physiological data different than the first symptom data and second symptom data;
applying the at least one first algorithm trained using machine learning to determine a first medical diagnosis corresponding to the user based on the first symptom data and the second symptom data;
determining there is a medical emergency corresponding to the first medical diagnosis, wherein determining that there is a medical emergency comprises processing the first symptom data and the second symptom data using at least one second algorithm trained to detect a medical emergency; and
sending a message regarding the medical emergency to one or more of emergency services, wherein the message sent to one or more emergency services comprises a location corresponding to the user.

11. The method of claim 10, wherein the first symptom data is encrypted by the user device and the second symptom data is encrypted by the second device.

12. The method of claim 10, further comprising:
causing the user device to present a display indicating the first medical diagnosis.

13. The method of claim 10, wherein the second symptom data comprises audio data generated by the user device.

14. The method of claim 13, further comprising:
transcribing the audio data of the second symptom data.

15. The method of claim 10, wherein the first symptom data and the second symptom data are selected from the group consisting of physiological data, blood data, image data, tissue data, body secretion data, breath analyzer data and motion data.

16. The method of claim 10, further comprising:
requesting payment information from the user device; and
receiving payment information from the user device.

17. The method of claim 16, wherein the payment information is secured using at least one blockchain algorithm.

18. The method of claim 1, wherein the at least one first algorithm trained using machine learning is a neural network.

19. The computing device of claim 6, wherein the one or more algorithms trained using machine learning is a neural network.

20. The method of claim 8, wherein the one or more algorithms trained using machine learning is a neural network.

21. The method of claim 10, wherein the at least one first algorithm trained using machine learning is a neural network.

\* \* \* \* \*